(12) United States Patent
Etkin et al.

(10) Patent No.: US 12,226,375 B1
(45) Date of Patent: *Feb. 18, 2025

(54) METHOD OF TREATMENT AND SELECTION OF PATIENTS BENEFITING FROM AGOMELATINE BASED ON EEG MEASUREMENTS

(71) Applicant: Alto Neuroscience, Inc., Los Altos, CA (US)

(72) Inventors: Amit Etkin, Los Altos, CA (US); Wei Wu, Los Altos, CA (US); Adam Savitz, Los Altos, CA (US); Joshua Jordan, Los Altos, CA (US); Maimon Rose, Los Altos, CA (US); Akshay Sujatha Ravindran, Los Altos, CA (US)

(73) Assignee: ALTO NEUROSCIENCE, INC., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/670,566

(22) Filed: May 21, 2024

Related U.S. Application Data

(60) Provisional application No. 63/518,742, filed on Aug. 10, 2023.

(51) Int. Cl.
 *A61K 31/165* (2006.01)
 *A61K 45/06* (2006.01)
 *A61P 25/24* (2006.01)

(52) U.S. Cl.
 CPC ............ *A61K 31/165* (2013.01); *A61K 45/06* (2013.01); *A61P 25/24* (2018.01)

(58) Field of Classification Search
 CPC ........ A61K 31/165; A61K 45/06; A61P 25/24
 See application file for complete search history.

(56) References Cited

U.S. PATENT DOCUMENTS

| 5,225,442 A | 7/1993 | Andrieux et al. |
| 2022/0387424 A1 | 12/2022 | Etkin et al. |

FOREIGN PATENT DOCUMENTS

| EP | 0447285 A1 | 9/1991 |
| WO | 2020081609 A1 | 4/2020 |

OTHER PUBLICATIONS

Salva et al., International Journal of Neuropsychopharmacology (2007), 10, 691-696) (Year: 2007).*

Laux G, Huttner Na; Vivaldi study group. Subgroup analysis of the non-interventional study Vivaldi: agomelatine in treatment-naïve patients, in combination therapy and after treatment switch. Int J Psychiatry Clin Pract. Jun. 2014;18(2):86-96—made of record on the IDS (Year: 2014).*

Desseilles M, Witte J, Chang TE, Iovieno N, Dording CM, Ashih H, Nyer M, Freeman MP, Fava M, Mischoulon D. Assessing the adequacy of past antidepressant trials: a clinician's guide to the antidepressant treatment response questionnaire. J Clin Psychiatry. Aug. 2011;72(8):1152-4. (Year: 2011).*

(Continued)

*Primary Examiner* — Clinton A Brooks
*Assistant Examiner* — Izabela Schmidt
(74) *Attorney, Agent, or Firm* — Blank Rome LLP

(57) ABSTRACT

This invention relates to the use of agomelatine (or a prodrug or salt thereof) in the treatment of major depressive disorder or bipolar disorder, including the selection of patients who would most benefit from agomelatine.

17 Claims, 9 Drawing Sheets

(56) References Cited

OTHER PUBLICATIONS

Skalski M, Mach A, Januszko P, Ryszewska-Pokraśniewicz B, Biernacka A, Nowak G, Pilc A, Poleszak E, Radziwoń-Zaleska M. Pharmaco-Electroencephalography-Based Assessment of Antidepressant Drug Efficacy—The Use of Magnesium Ions in the Treatment of Depression. J Clin Med. Jul. 15, 2021;10(14):3135. (Year: 2021).*
Potměšil P. What combinations of agomelatine with other antidepressants could be successful during the treatment of major depressive disorder or anxiety disorders in clinical practice? Ther Adv Psychopharmacol. Jul. 7, 2019;9-11 (Year: 2019).*
Trevor R. Norman & James S. Olver (2019) Agomelatine for depression: expanding the horizons? Expert Opinion on Pharmacotherapy, 20:6, 647-656 (Year: 2019).*
Dubocovich ML. Agomelatine targets a range of major depressive disorder symptoms. Curr Opin Investig Drugs. Jul. 2006;7(7):670-80. PMID: 16869122 (Year: 2006).*
Saeedi Physical and Engineering Sciences in Medicine (2020) 43:1007-1018 (Year: 2020).*
(Dahale AB, Narayanaswamy JC, Venkatasubramanian G, Bagewadi VI. Gen Hosp Psychiatry. Jan.-Feb. 2014;36(1):e3 (Year: 2014).*
Salva et al., International Journal of Neuropsychopharmacology (2007), 10, 691-696) (Year: 2007) (Year: 2007).*
Dubocovich ML. Agomelatine targets a range of major depressive disorder symptoms. Curr Opin Investig Drugs. Jul. 2006;7(7):670-80. PMID: 16869122 (Year: 2006) (Year: 2006).*
Laux G, Huttner NA; Vivaldi study group. Subgroup analysis of the non-interventional study Vivaldi: agomelatine in treatment-naïve patients, in combination therapy and after treatment switch. Int J Psychiatry Clin Pract. Jun. 2014;18(2):86-96—made of record on the IDS (Year: 2014) (Year: 2014).*
(Dahale AB, Narayanaswamy JC, Venkatasubramanian G, Bagewadi VI. Gen Hosp Psychiatry. Jan.-Feb. 2014;36(1):e3 (Year: 2014) (Year: 2014).*
Watts, D., Pulice, R.F., Reilly, J. et al. Predicting treatment response using EEG in major depressive disorder: A machine-learning meta-analysis. Transl Psychiatry 12, 332 (2022). (Year: 2022).*
Lau ZJ, Pham T, Chen Sha, Makowski D. Brain entropy, fractal dimensions and predictability: A review of complexity measures for EEG in healthy and neuropsychiatric populations. Eur J Neurosci. Oct. 2022;56(7):5047-5069. doi: 10.1111/ejn.15800. Epub Sep. 2, 2022. PMID: 35985344; PMCID: PMC9826422 (Year: 2022).*
Cukic at al., Cognitive Neurodynamics (2020) 14:443-455 (Year: 2020).*
Laux et al., Clin Pract. 2014, 18(2):86-96.
Norman et al., Exp. Op. Pharmacother., 20(6):647-656 (2019).
International Search Report and Written Opinion in PCT/US2024/030416 on Sep. 4, 2024.
Corruble, Emmanuelle , et al., "Efficacy of Agomelatine and Escitalopram on Depression, Subjective sleep and Emotional Experiences in Patients with Major Depressive Disorder: a 24-wk Randomized, Controlled, Double-blind Trial,", International Journal of Neuropsychopharmacology, 2013, 16:2219-2234, XP055729756.
Cukic, Milena , et al., "When Heart Beats Differently in Depression: A Review of HRV Measures,", arxiv.org, Cornell University Library, 201 Olin Library Cornell University Itacha, NY 14853, 2021, pp. 3-5, XP091077614.
Dubocovich, Margarita L, "Drug Evaluation: Agomelatine Targets a Range of Major Depressive Disorder Symptoms,", Current Opinion in Investigational Drugs, 2006, 7:7:670-680, XP008078929.
Pandi-Perumal, Seithikurippu R, et al., "Bidirectional Communication Between Sleep and Circadian Rhythms and Its Implications for Depression: Lessons from Agomelatine,", Progress in Neurobiology, 2009, 88:264-271, XP026337933.
Fineberg, N.A., et al., "p. 2.102 Effect of Agomelatine on the Sleep EEP in Patients with Major Depressive Disorder (MMD),", European Neuropsychophamacology, Elsevier Science Publishers BV, Amsterdam, NL, 2015, 15:S435-S436, XP005514625.
Quera-Salva, Maria-Antonia , et al., "Impact of the Novel Antidepressant Agomelatine on Disturbed Sleep-wake Cycles in Depressed Patients", Hum. Psychopharmacol Clin Exp, 2010, 25:222-229, XP071720525.
Wichniak, Adam , et al., "Sleep as a Biomarker for Depression,", International Review of Psychiatry, 2013, 25:5:632-645, XP093131643.
Cukic (Cognitive Neurodynamics (2020) 14:443-455) (Year: 2020).
Dahale (General Hospital Psychiatry 36 (2014) e3. p. 1) (Year: 2014).
Safayari (Medicine in Novel Technology and Devices 12 (2021) 100102. p. 1-16) (Year: 2021).

* cited by examiner

METHOD OF TREATMENT AND SELECTION OF PATIENTS BENEFITING FROM AGOMELATINE BASED ON EEG MEASUREMENTS

This application claims the benefit of U.S. Provisional Application No. 63/518,742, filed Aug. 10, 2023, which is incorporated by reference.

FIELD OF THE INVENTION

This invention relates to the use of agomelatine (or a prodrug or salt thereof) in the treatment of major depressive disorder or bipolar disorder, including the selection of patients who would most benefit from agomelatine.

BACKGROUND OF THE INVENTION

Clinical care for depression involves assessment and diagnosis based on a set of clinician-assessed and patient-reported symptoms such as depressed mood, anhedonia, appetite changes, sleep and psychomotor changes but notably no biological or quantitative behavioral variables. When an assessment such as a magnetic resonance imaging (MRI) scan or a blood test is performed, it is to rule out non-psychiatric causes of depression which may necessitate treatments other than an antidepressant medication, including causes such a hypothyroidism, dementia or metabolic disruptions. After diagnosing a patient with depression, a clinician may then prescribe one of multiple antidepressant treatments, which primarily includes drugs such as selective serotonin reuptake inhibitors (SSRIs), serotonin norepinephrine reuptake inhibitors (SNRIs), and norepinephrine dopamine reuptake inhibitors (NDRIs), or atypical antidepressants. Notably, however, selection of antidepressant medication is done purely by trial-and-error, with no biological or quantitative behavioral measures to inform medication choice. Typically, SSRIs are selected as the first line treatment based on their general tolerability, but not because they are known to be more effective for the broader patient population, nor more effective for that particular patient. Most patients, however, fail to respond adequately to the first medication (Trivedi et al., *Am J Psychiatry*, 2006, 163 (1): 28-4, doi: 10.1176/appi.ajp. 163.1.2, PMID 16390886), at which point selection of the next medication again follows a trial-and-error process. Indeed, it has been found that on average, failing one SSRI does not necessarily predict a different response to another SSRI versus an SNRI or NDRI (Rush et al., *N Engl J Med.* 2006, 354:1231-1242). Further there is no clear guidance if one should augment an antidepressant with an insufficient response or switch to a different antidepressant since both options have similar outcomes. As such, clinical assessments typical of clinical care interactions do not provide information sufficiently useful for selection of subsequent medication trials, and therefore external information required by the clinician to improve medication selection is not available.

The economic, societal and personal cost of depression is very large, with depression being the leading cause of disability worldwide. This is even more pronounced for treatment-resistant depression (Amos et al., *J Clin Psychiatry*, 2018, 79:2, PMID 29474009), thus suggesting that finding the best medication for an individual early in the course of treatment would provide many downstream benefits to the patient and society at large.

One medication that may differ in its mechanisms and clinical effects from conventional SSRIs/SNRIs is agomelatine (N-[2-(7-methoxynaphthalen-1-yl)ethyl]acetamide) which, unlike other conventional antidepressants, stimulates melatonin receptors and blocks serotonin $5-HT_{2C}$ receptors. Agomelatine was developed as a monotherapy antidepressant (i.e. given to individuals who are not on a conventional antidepressant), and was ultimately approved in Europe and Australia. However, there is substantial controversy about the efficacy of this drug, owing to its reported small and variable benefit over placebo. Norman et al., *Exp. Op. Pharmacother.*, 20 (6): 647-656 (2019). In fact, the drug was developed as a monotherapy antidepressant in the United States, but its development was ultimately discontinued due to insufficient evidence of efficacy. The cause of the variability in observed efficacy of agomelatine is unknown.

Furthermore, little is known about the efficacy of agomelatine if given as an adjunct to or as an augmentation agent in addition to a conventional antidepressant to which the patient had failed to respond but is continuing to take at the time adjunctive treatment is initiated. Augmentation, adjunctive, or "add-on", treatment is an important part of the depression treatment paradigm (Potmesil, *Ther Adv Psychopharmacol*, 2019, 9:1-11, PMID 31312426). However, only antipsychotic medications have been approved for adjunctive use in depression but carry substantial side effect burdens and are poorly tolerated (Wen et al., *Braz J Med Biol Res.* 2014, 47(7): 605-16, doi: 10.1590/1414-431x20143672, PMID 24919175; Yan et al., *Psychol Med.* 2022, 52(12): 2224-2231, doi: 10.1017/S0033291722001246, PMID 35993319). There are a handful of open label agomelatine treatment studies employing adjunctive treatment with agomelatine (Laux et al., *Clin Pract.* 2014, 18 (2): 86-96), but it is uncertain from these results whether this response is likely to be different from placebo or an alternative treatment nor what characterizes the subpopulation of patients who respond robustly to the drug.

Based on the synergistic action of melatonin agonism and 5-HT2c antagonism on hypothalamic regulation of circadian rhythms (de Bodinat et al., *Nat Rev Drug Discov*, 2010, 9(8): 628-42, PMID 20577266) it has been argued that agomelatine may have particular utility in the treatment of depression with prominent sleep and/or circadian rhythm disruptions (Popoli et al., *CNS Drugs.* 2009, 23 Suppl 2:27-34; Jakovljevic et al., *Psychiatr Danub.* 2011; 23:2-9). For example, agomelatine has been shown to improve sleep measures assessed using actigraphic measurements, in contrast to an SSRI which did not change these measures (Kasper et al., *J Clin Psychiatry*, 2010; 71:109-120; Quera Salva et al., *Int J Neuropsychopharmacol*, 2007, 10:691-696; Quera-Salva et al., *Hum Psychopharmacol*, 2010, 25:222-229). These effects included increasing the deep to total sleep ratio (Quera Salva 2007, supra; Quera Salva 2010, supra). Deep sleep, also known as slow-wave sleep, is thought to be a particularly restorative aspect of sleep and is implicated in processes such as memory consolidation and allowing the brain to recover from its daily activities (Rasch et al., *Physiol Rev*, 2013, 93:681-766). Deep sleep is also known to be reduced in depression in general (Arfken et al., *J Affect Disord*, 2014, 156:36-45; Wichniak et al., *Int Rev Psychiatry*, 2013, 25:632-645; Riemann et al., *Neuropsychopharmacology*, 2020, 45:74-89). Agomelatine has also been found to be superior to an SSRI in improving performance on a trail making task (Aydin et al., European Psychiatry, 2016, 33: S405), and in general antidepressants such as SSRIs have little if any effect on a broad range of cognitive measures including the trail making task (Shilyansky et al., *Lancet Psychiatry*, 2016, 3 (5): 425-435).

Nonetheless, these effects of agomelatine on sleep or cognition do not in themselves define characteristics of patients who would respond robustly to the drug. For example, while agomelatine and melatonin have been found to phase advance circadian rhythm due to their melatonergic agonism (Leproult et al., *Clin Endocrinol* (Oxf), 2005, 63 (3): 298-304, PMID 16117817; Kräuchi et al., *Am J Physiol.*, 1997, 272 (4 Pt 2): R1178-88, PMID 9140018), melatonin is not an effective antidepressant (Hansen et al., *Eur Neuropsychopharmacol*, 2014, 24 (11): 1719-28, PMID 25224106; De Crescenzo et al., *Acta Psychiatr Scand*, 2017, 136 (6): 549-558, PMID 28612993). In fact, the limited research on predictors of agomelatine response suggests the opposite—that earlier circadian phase predicts better response. It has been found that patients with greater morningness on a circadian preference survey prior to treatment respond better to agomelatine (Corruble et al., *Chronobiology Int'l*, 2014, 31 (2): 283-289). Morningness on this or the same or similar surveys has been consistently and strongly linked to an earlier circadian phase as measured through actigraphy (Jones et al., *Nat Commun*, 2019, 10 (1): 343, PMID 30696823; Schneider et al., *Chronobiol Int*, 2022, 39 (2): 205-220, PMID 34806526; Bailey et al., *Chronobiol Int*, 2001, 18 (2): 249-61, PMID 11379665). Thus, a study aiming to predict agomelatine response points to better outcome in earlier circadian phase patients, while inferences made based on the pharmacodynamic effects of agomelatine (albeit shared with melatonin, an ineffective antidepressant) point to better outcome in later circadian phase patients. These contradictory findings are within the domain of circadian phase measures. Much less is known about other facets of brain function, such as those that could be tapped into by recording brain activity or through behavioral testing. Prior to the present invention, it was therefore uncertain which patients are most responsive to agomelatine (i.e., those for whom it would be critical to target a drug with otherwise questionable efficacy across unselected depression patients). This state of uncertainty is further amplified when considering the use of agomelatine as an adjunct to a failed conventional antidepressant, about which little is known clinically.

Despite agomelatine's unique mechanisms of action, SSRIs continue to be the most common medication prescribed in clinical practice through multiple rounds of failed medication trials, and when deviations are made it is to the use of SNRIs and NDRIs alone or in combination with SSRIs, or addition of an atypical antipsychotic (Wu et al., *PLOS One*, 2019, 14: e0220763). By contrast, agomelatine is the least-prescribed of conventional antidepressants in markets where it is approved (Forns et al., *J Affect Disord*, 2019, 249:242-252). Moreover, inasmuch as any measurement is done of patients as part of clinical care, clinicians only have access to patient-reported or clinician-observed clinical signs and symptoms. Thus, clinicians do not have a basis upon which to select any one medication over another and would hence not be able to discern who would best respond to agomelatine. As such, no measures exist for identifying agomelatine-responsive patients prior to treatment. Definition of such signals would have a major impact on the ability to prescribe agomelatine in a manner that best aligns its action with clinical benefits for a defined subpopulation of patients with depression or a comorbid illness.

SUMMARY OF THE INVENTION

Surprisingly, it has now been found that the effects of agomelatine, or a prodrug thereof or a pharmaceutically acceptable salt thereof, can be predicted by a pattern of brain activity as recorded through electroencephalography. The present invention therefore includes the use of one or more of these electroencephalogram (EEG) measures as a method by which to identify those patients who would most benefit from agomelatine treatment.

One embodiment is a method of treating major depressive disorder (MDD) or the depressive phase of bipolar disorder in a patient or treating depressive symptoms in a patient having post-traumatic stress disorder (PTSD), where the patient is being treated with one or more antidepressants other than agomelatine (or a prodrug or salt thereof) but has failed to adequately respond to the one or more antidepressants. Where the patient, prior to initiation of agomelatine treatment, exhibits high EEG sample entropy using low gamma frequency range (30-40 Hz) electroencephalography, the method includes administering a therapeutically effective amount of (a) agomelatine, a prodrug thereof, or a pharmaceutically acceptable salt thereof and (b) the one or more antidepressants. In other words, the agomelatine (or a prodrug thereof or salt thereof) is administered as an adjunctive therapy to one or more currently prescribed antidepressants, where the patient previously failed to respond to the one or more antidepressants. In one embodiment, the EEG measures are taken with resting eyes closed (REC). In one embodiment, the patient suffers from major depressive disorder and PTSD.

One embodiment is a method of treating the depressive phase of bipolar disorder in a patient, where the patient is being treated with one or more mood stabilizers and/or one or more antidepressants other than agomelatine (or a prodrug or salt thereof), but has failed to adequately respond to the one or more mood stabilizers and/or antidepressants. Where the patient, prior to initiation of agomelatine treatment, exhibits high EEG sample entropy using low gamma frequency range (30-40 Hz) electroencephalography, the method includes administering a therapeutically effective amount of (a) agomelatine, a prodrug thereof, or a pharmaceutically acceptable salt thereof and (b) the one or more mood stabilizers and/or one or more antidepressants. In other words, the agomelatine (or a prodrug or salt thereof) is administered as an adjunctive therapy to one or more currently prescribed mood stabilizers and/or antidepressants, where the patient previously failed to respond to the one or more antidepressants. In one embodiment, the EEG measures are taken with resting eyes closed (REC). In one embodiment, the patient suffers from major depressive disorder and PTSD.

Yet another embodiment is a method of treating major depressive disorder or the depressive phase of bipolar disorder in a patient or treating depressive symptoms in a patient having PTSD, where the patient, prior to initiation of treatment with agomelatine (or a prodrug or salt thereof) and the one or more antidepressants, exhibits high EEG sample entropy using low gamma frequency range (30-40 Hz) electroencephalography. The method includes administering a therapeutically effective amount of (a) agomelatine, a prodrug thereof, or a pharmaceutically acceptable salt thereof and (b) one or more antidepressants (e.g., one antidepressant) other than agomelatine (or a prodrug or salt thereof). In one embodiment, the EEG measures are taken with resting eyes closed (REC). In one embodiment, the patient prior to treatment with the combination of agomelatine (or a prodrug or salt thereof) and the one or more antidepressants was not treated with an antidepressant. In one embodiment, the patient suffers from major depressive disorder and PTSD.

Yet another embodiment is a method of treating the depressive phase of bipolar disorder in a patient, where the patient, prior to initiation of treatment with (a) agomelatine (or a prodrug or salt thereof) and (b) the one or more antidepressants and/or mood stabilizers, exhibits high EEG sample entropy using low gamma frequency range (30-40 Hz) electroencephalography. The method includes administering a therapeutically effective amount of (a) agomelatine, a prodrug thereof, or a pharmaceutically acceptable salt thereof and (b) one or more mood stabilizers and one or more antidepressants (e.g., one antidepressant) other than agomelatine. In one embodiment, the patient prior to treatment with the combination of (a) agomelatine (or a prodrug or salt thereof) and (b) the one or more mood stabilizers and/or antidepressants was not treated with a mood stabilizer and/or antidepressant. In one embodiment, the EEG measures are taken with resting eyes closed (REC).

In one embodiment of any of the methods described herein, the one or more antidepressants are selected from a selective serotonin reuptake inhibitor (SSRI), serotonin norepinephrine reuptake inhibitor (SNRI), bupropion or a pharmaceutically acceptable salt thereof, or any combination of any of the foregoing.

Yet another embodiment is a method of treating major depressive disorder or the depressive phase of bipolar disorder in a patient or treating depressive symptoms in a patient having PTSD, where the patient, prior to initiation of agomelatine treatment (or a prodrug or salt thereof), exhibits high EEG sample entropy using low gamma frequency range (30-40 Hz) electroencephalography. The method includes administering a therapeutically effective amount of agomelatine, a prodrug thereof, or a pharmaceutically acceptable salt thereof. In one embodiment, the EEG measures are taken with resting eyes closed (REC). In one embodiment, the patient previously failed to respond to one or more antidepressants other than agomelatine (or a prodrug or salt thereof), and upon initiation of agomelatine, treatment with the prior one or more antidepressants are discontinued. In an alternative embodiment, the patient previously failed to respond to one or more antidepressants other than agomelatine (or a prodrug or salt thereof), and upon initiation of agomelatine, treatment with the prior one or more antidepressants are continued. In yet another embodiment, the patient was not previously treated with one or more antidepressants and/or mood stabilizers, and upon initiation of agomelatine (or a prodrug or salt thereof), treatment with one or more antidepressants and/or mood stabilizers is also initiated.

Yet another embodiment of the invention is a method of maintaining euthymia in a patient having bipolar disorder (such as bipolar I disorder or bipolar II disorder), where the patient, prior to initiation of agomelatine treatment (or a prodrug or salt thereof), exhibits high EEG sample entropy using low gamma frequency range (30-40 Hz) electroencephalography. The method includes administering an effective amount of agomelatine, a prodrug thereof, or a pharmaceutically acceptable salt thereof to maintain euthymia in the patient. In one embodiment, the EEG measures are taken with resting eyes closed (REC). In one embodiment, the patient previously failed to respond to one or more mood stabilizers or antidepressants other than agomelatine (or a prodrug or salt thereof), and upon initiation of agomelatine (or a prodrug or salt thereof), treatment with the prior one or more mood stabilizers and antidepressants are discontinued. In an alternative embodiment, the patient previously failed to respond to one or more mood stabilizers or antidepressants other than agomelatine (or a prodrug or salt thereof), and upon initiation of agomelatine (or a prodrug or salt thereof), treatment with the prior one or more mood stabilizers are continued (but not the antidepressants). In yet another embodiment, the patient was not previously treated with one or more antidepressants and/or mood stabilizers, and upon initiation of agomelatine (or a prodrug or salt thereof), treatment with one or more antidepressants and/or mood stabilizers is also initiated.

In one embodiment of any of the methods described herein, the patient exhibits high EEG sample entropy at the Pz electrode (according to the 10-20 system of electrode placement).

In one embodiment of any of the methods described herein, the EEG measures are taken with resting eyes closed.

In one embodiment of any of the methods described herein, the patient suffers from moderate to severe major depressive disorder.

In one embodiment, the agomelatine, a prodrug thereof, or a pharmaceutically acceptable salt thereof is administered once daily at night.

In one embodiment of any of the methods described herein, the method comprises orally administering from about 25 to about 50 mg agomelatine, a prodrug thereof, or a pharmaceutically acceptable salt thereof (based on agomelatine free base) per day (preferably nightly). In one embodiment, the method comprises orally administering about 25 mg agomelatine, a prodrug thereof, or a pharmaceutically acceptable salt thereof (based on agomelatine free base) per day (preferably nightly). In another embodiment, the method comprises orally administering about 50 mg agomelatine, a prodrug thereof, or a pharmaceutically acceptable salt thereof (based on agomelatine free base) per day. In yet another embodiment, the method comprises orally administering about 30 mg agomelatine, a prodrug thereof, or a pharmaceutically acceptable salt thereof (based on agomelatine free base) per day.

In one embodiment of any of the methods described herein, the method comprises orally administering from about 25 to about 50 mg agomelatine per day. In a preferred embodiment, the method comprises orally administering from about 25 to about 50 mg agomelatine per day nightly.

In one embodiment of any of the methods described herein, the method comprises orally administering about 25 mg agomelatine per day. In a preferred embodiment, the method comprises orally administering about 25 mg agomelatine per day nightly.

In one embodiment of any of the methods described herein, the method comprises orally administering about 50 mg agomelatine per day. In a preferred embodiment, the method comprises orally administering about 50 mg agomelatine per day nightly.

In one embodiment of any of the methods described herein, the agomelatine is administered once daily at bedtime.

Yet another embodiment of the invention is a method of treating major depressive disorder (MDD), or the depressive phase of bipolar disorder (such as bipolar I disorder or bipolar II disorder) in a patient or treating depressive symptoms in a patient having post-traumatic stress disorder (PTSD) comprising:
  (a) analyzing one or more indicators of the responsiveness of the patient to agomelatine (or a prodrug or a pharmaceutically acceptable salt thereof) as a treatment for major depressive disorder or the depressive phase of bipolar disorder (such as bipolar I disorder or bipolar II disorder), or depressive symptoms in a patient having PTSD; and (b) administering (e.g., orally) to the patient an effective amount of agomelatine, a prodrug thereof, or a pharmaceutically acceptable salt thereof (e.g., about 25 to about 50 mg agomelatine daily, such as 25 mg agomelatine once daily or 50 mg agomelatine once daily (e.g., once nightly)), where the patient is determined to be responsive to agomelatine (or a prodrug or salt thereof) based on the one or more indicators. The one or more indicators can be selected from EEG measures of entropy or complexity, and any combination of any of the foregoing.

Yet another embodiment of the invention is a method of maintaining euthymia in a patient having bipolar disorder (such as bipolar I disorder or bipolar II disorder) comprising:
(a) analyzing one or more indicators of the responsiveness of the patient to agomelatine (or a prodrug or a pharmaceutically acceptable salt thereof) as a method for maintain euthymia in a patient suffering from bipolar disorder (such as bipolar I disorder or bipolar II disorder); and
(b) administering (e.g., orally) to the patient an effective amount of agomelatine, a prodrug thereof, or a pharmaceutically acceptable salt thereof (e.g., about 25 to about 50 mg agomelatine daily, such as 25 mg agomelatine once daily or 50 mg agomelatine once daily (e.g., once nightly)), where the patient is determined to be responsive to agomelatine (or a prodrug or salt thereof) based on the one or more indicators. The one or more indicators can be selected from EEG measures of entropy or complexity, and any combination of any of the foregoing (such as those described herein). In one embodiment, the patient previously failed to respond to one or more mood stabilizers or antidepressants other than agomelatine (or a prodrug or salt thereof), and upon initiation of agomelatine (or a prodrug or salt thereof), treatment with the prior one or more mood stabilizers and antidepressants are discontinued. In an alternative embodiment, the patient previously failed to respond to one or more mood stabilizers or antidepressants other than agomelatine (or a prodrug or salt thereof), and upon initiation of agomelatine (or a prodrug or salt thereof), treatment with the prior one or more mood stabilizers are continued. In yet another embodiment, the patient was not previously treated with one or more antidepressants and/or mood stabilizers, and upon initiation of agomelatine (or a prodrug or salt thereof), treatment with one or more antidepressants and/or mood stabilizers is also initiated.

The EEG measures can be selected from a range of measures that index neural complexity (see FIG. 1). These include measures of complexity, such as Higuchi's Fractal Dimension, Katz's Fractal Dimension, Detrended Fluctuation Analysis, Largest Lyapunov Exponent, Approximate Entropy, Sample Entropy, Multiscale Entropy, Modified Multiscale Entropy, and Aperiodic Exponent. In one embodiment, the EEG measure is sample entropy.

In one embodiment, the EEG measures indicate that the patient exhibits higher sample entropy.

In one embodiment, the patient (e.g., a patient suffering from major depressive disorder) has previously been treated with one or more antidepressants but failed to achieve an adequate response to them and continues to be treated with the one or more antidepressants even after agomelatine treatment (or a prodrug or salt thereof) is begun. In other words, agomelatine (or a prodrug or salt thereof) is provided as a monotherapy, an adjunctive therapy to the one or more antidepressants, or a co-therapy with one or more antidepressants different from that previously administered to the patient. In one embodiment, the one or more antidepressants do not include a monoamine oxidase inhibitor (MAOI) or a tricyclic antidepressant. In another embodiment, the one or more antidepressants are selected from (i) serotonin reuptake inhibitors, (ii) serotonin norepinephrine reuptake inhibitors, (iii) bupropion (or a pharmaceutically acceptable salt thereof, such as bupropion hydrochloride) optionally with other medications (such as dextromethorphan), and (iv) any combination of any of the foregoing. The patient may suffer from major depressive disorder or bipolar disorder.

In another embodiment, the one or more indicators in step (a) are analyzed with stored historical subject data containing data from a plurality of subjects having major depressive disorder or bipolar disorder (such as bipolar I disorder or bipolar II disorder) who received treatment with agomelatine, a prodrug thereof, or a pharmaceutically acceptable salt thereof. The data may include for a plurality of the subjects, the efficacy of the agomelatine treatment (or a prodrug or salt thereof) and one or more of the indicators used to analyze the patient.

In one embodiment, step (a) includes determining an agomelatine efficacy likelihood score (e.g., z-score) for the patient based on the stored historical subject data, and step (b) comprises administering to the patient an effective amount of agomelatine, a prodrug thereof, or a pharmaceutically acceptable salt thereof, where the patient is determined to be responsive to agomelatine based on the likelihood score. The likelihood score may be binary (that is, 0 or 1 (categorical)) or continuous. In one embodiment, the likelihood score is bounded, for example, any value from 0 to 1.

This method can be performed on a patient newly diagnosed with major depressive disorder or bipolar disorder (such as bipolar I disorder or bipolar II disorder). This method can also be performed on a patient being treated for major depressive disorder or bipolar disorder (such as bipolar I disorder or bipolar II disorder) where the treatment does not involve agomelatine (or a prodrug or salt thereof).

In one embodiment of any of the methods described herein, the EEG measures are taken with resting eyes closed.

BRIEF DESCRIPTION OF THE DRAWINGS

For a more complete understanding of the present invention, including features and advantages, reference is now made to the detailed description of the invention along with the accompanying figures.

DETAILED DESCRIPTION OF THE INVENTION

Figure 1A:
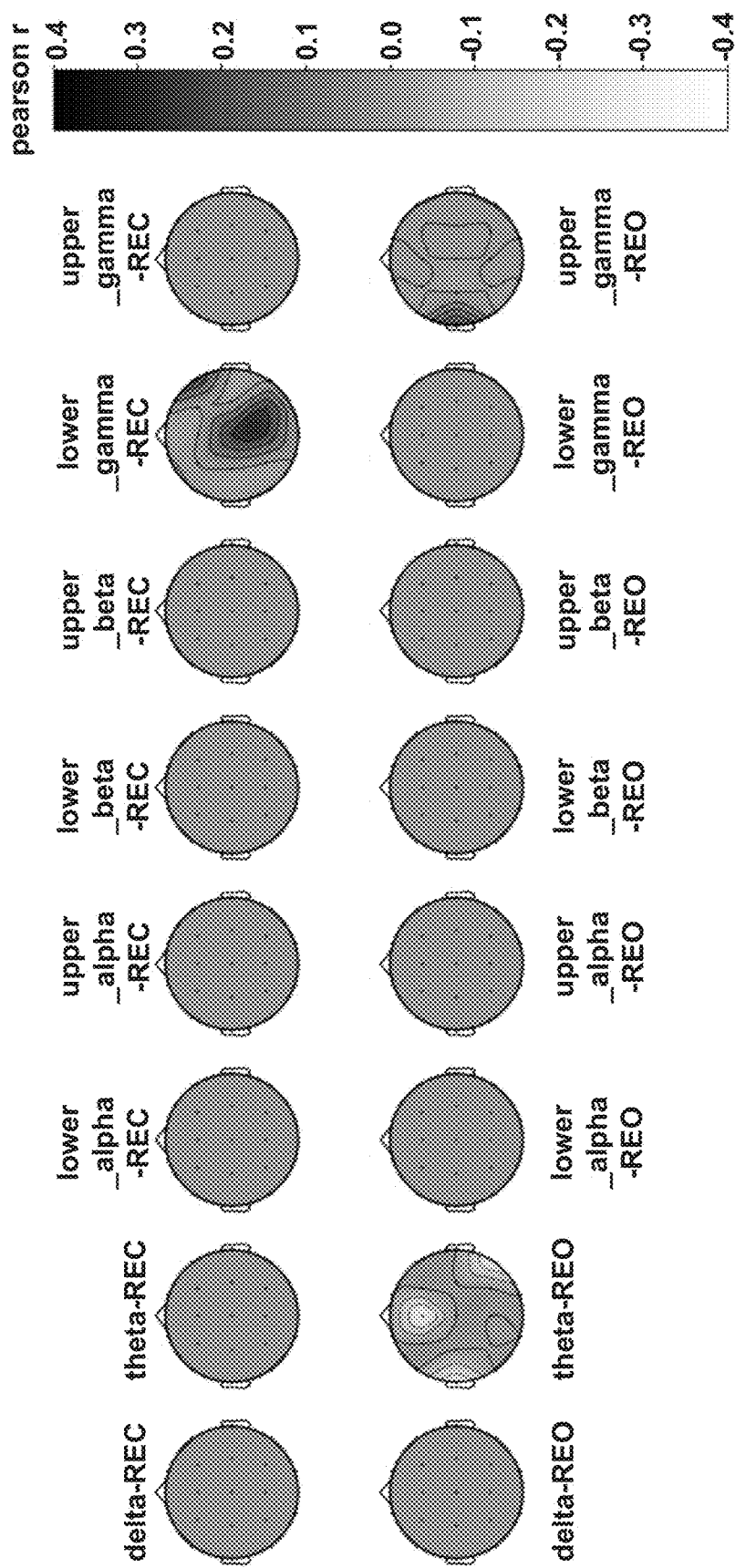
FIGS. 1A, 1B and 1C show a $p<0.05$ thresholded topographical map of channel-level correlations between sample entropy and percentage change in MADRS scores from baseline to week 4, 6, or 8 (subsections A, B, and C, respectively), of treatment with agomelatine. REC-resting eyes closed, REO-resting eyes open. Frequency bands are: delta (2-4 Hz), theta (4-7 Hz), lower alpha (8-10 Hz), upper alpha (10-12 Hz), lower beta (13-20 Hz), upper beta (20-30 Hz), lower gamma (30-40 Hz), upper gamma (40-50 Hz).

Agomelatine (N-[2-(7-methoxynaphthalen-1-yl) ethyl] acetamide) and its synthesis are described in European Patent Publication No. 447285 A1 and U.S. Pat. No. 5,225,442, both of which are hereby incorporated by reference in their entirety. Agomelatine is a melatonin agonist (i.e., $MT_1$ and $MT_2$ receptor-site agonism) and a $5HT_{2e}$ antagonist.

The term "prodrug" refers to a precursor of agomelatine that, following administration to a subject, yields agomelatine in vivo, such as via a chemical or physiological process such as solvolysis or enzymatic cleavage, or under physiological conditions (e.g., a prodrug on being brought to physiological pH is converted to agomelatine). Prodrugs of agomelatine may be prepared by modifying functional groups present on the compound in such a way that the modifications are cleaved, in vivo when the prodrug is administered to a subject. The modifications typically are achieved by synthesizing the agomelatine with a prodrug substituent. Prodrugs may be prepared as described in (i) Bundegaard, H. "Design of Prodrugs" p. 1-92, Elesevier, New York-Oxford (1985), (ii) Methods in Enzymology, Vol. 42, p. 309-396, edited by K. Widder, et al. (Academic Press, 1985), (iii) A Textbook of Drug Design and Development, $3^{rd}$ Ed., Tailor & Francis Inc., edited by Krogsgaard-Larsen et al., Chapter 14 "Design and Application of Prodrugs," by Larsen et al., p. 460-514 (2002), (iv) H. Bundgaard, Advanced Drug Delivery Reviews, 8:1-38 (1992), (v) N. M. Nielsen, et al., Journal of Pharmaceutical Sciences, 77:285-298 (1988), and (vi) N. Kakeya, et al., Chem. Pharm. Bull., 32:692-698 (1984), each of which is specifically incorporated herein by reference. In one embodiment, the prodrug substituent directs the compound to the lymphatic system. Such prodrug substituents are described in International Publication Nos. WO 2019/046491 and WO 2021/159021, each of which is hereby incorporated by reference. Such prodrug substituents may be conjugated to agomelatine through, for example, the methoxy or acetamide group of agomelatine.

The terms major depressive disorder, bipolar disorder, bipolar I disorder, and bipolar II disorder are intended to be as defined in the Diagnostic and Statistical Manual of Mental Disorders (DSM-5), which is hereby incorporated by reference. The severity of depression can be measured by the Montgomery-Asberg Depression Rating Scale (MADRS), Patient Health Questionnaire-9 (PHQ-9), Clinical Global Impression—severity Scale (CGI-S), Hamilton Depression Rating Scale (HDRS), or any combination of any of the foregoing.

The terms "treat," "treatment," and "treating" in the context of the administration of a therapy to a patient refers to the reduction or inhibition of the progression and/or duration of a disease or condition, the reduction or amelioration of the severity of a disease or condition, and/or the amelioration of one or more symptoms thereof resulting from the administration of one or more therapies.

In certain embodiments, the patient had an inadequate response to other antidepressant therapy (i.e., one or more antidepressants other than agomelatine or a prodrug or salt thereof). In one embodiment, "inadequate response" as used herein refers to a patient experiencing a less than 50% reduction in depressive symptom severity from the start of initiating treatment. Typically, the inadequate response is during a current/active episode of the depression. In some embodiments, an inadequate response refers to a patient experiencing 0 to less than about 50% reduction in depressive symptom severity from the start of initiating treatment. In some embodiment, an inadequate response refers to a patient experiencing (a) less than about 50% reduction in depressive symptom severity from the start of initiating treatment and (b) at least a certain level of symptoms, such as a PHQ9 of at least 10. A patient's response may be measured by one or more scales described herein and/or by physician/clinical judgment. In some embodiments, an inadequate response is measured by ATRQ (the antidepressant treatment response questionnaire), MADRS, PHQ-9, CGI-S, or HDRS.

The term "antidepressant" unless indicated otherwise includes selective serotonin reuptake inhibitors (SSRIs) (e.g., fluoxetine, escitalopram, citalopram, and sertraline), selective serotonin and norepinephrine reuptake inhibitors (SNRIs) (e.g., venlafaxine, duloxetine, and milnacipran), norepinephrine and dopamine reuptake inhibitors (e.g., bupropion), atypical antidepressants, and any combination of any of the foregoing. In one embodiment, the antidepressant is selected from an SSRI, SNRI, or bupropion. In another embodiment, antidepressant is selected from an SSRI (other than fluvoxamine), SNRI, or bupropion.

The "mood stabilizer" referenced herein may be lithium carbonate, lithium orotate, lithium salt, valproic acid, divalproex sodium, propranolol, clonazepam, sodium valproate, lamotrigine, carbamazepine, gabapentin, oxcarbazepine, topiramate, a pharmaceutically acceptable salt thereof, or any combination of any of the foregoing.

As used herein, the term "high EEG sample entropy" refers to an EEG signal in which sample entropy is in the higher range of the distribution in patients, e.g., relative to the mean entropy value in a healthy population. In one embodiment, EEG sample entropy is calculated as a standardized score (e.g., z-scores, T-scores, Standard Scores, Scaled Scores, Percentile rank, or Stanine scores) normalizing the patient against a healthy population (e.g., with respect to age, gender, or education). For example, the subject may have EEG sample entropy more than the mean of a similar healthy subject with a z-score more than zero, more than $z=0.25$, $z=0.5$, $z=0.75$, $z=1$, $z=1.5$, or $z=2$ (e.g., with a z-score of from about 0.5 or 0.75 to about 1 or 2, or a z-score of from about 0.75 or 1 to about 2). In one embodiment, a patient is considered to have higher entropy when the z-score is at least 0, 0.5, 1.0, 1.5, or 2.0 (e.g., at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0). In one embodiment, the raw EEG data from a patient is first loaded and subjected to preprocessing steps including resampling, applying notch and bandpass filtering. Subsequently, the data undergoes bad-channel interpolation and artifact rejection, and is then re-referenced, quality-checked, and stored for analysis.

As used herein, the terms "subject" and "patient" are used interchangeably and refer to a human patient unless indicated otherwise. In one embodiment, the patient has moderate to severe major depressive disorder. In another embodiment, the patient has moderate to severe major depressive disorder and is currently being treated with a SSRI, SNRI, or bupropion (e.g., bupropion or a pharmaceutically acceptable salt thereof in combination with another medication, such as dextromethorphan) for at least 6 weeks with no dose modifications in the past 2 weeks. In yet another embodiment, the patient has moderate to severe major depressive disorder and has failed to adequately respond to the current antidepressant medication which includes a SSRI, SNRI, or bupropion (e.g., bupropion or a pharmaceutically acceptable salt thereof in combination with another medication, such as dextromethorphan) for at least 6 weeks with no dose modifications in the past 2 weeks.

EEG measures indexing neural complexity include, but are not limited to, Higuchi's Fractal Dimension, Katz's Fractal Dimension, Detrended Fluctuation Analysis, Largest Lyapunov Exponent, Approximate Entropy, Sample Entropy, Multiscale Entropy, Modified Multiscale Entropy, and Aperiodic Exponent. Such measures are described in Lau et al., *Eur J Neurosci*, 2022, 56 (7): 5047-5069; doi: 10.1111/ejn. 15800; PMID 35985344), which is hereby incorporated by reference.

Treatment Methods

The agomelatine (or a prodrug or salt thereof) may be administered by any route, such as orally, rectally, percutaneously or by parenteral injection. A preferred route of administration is oral. The agomelatine (or a prodrug or salt thereof) may be administered in the form of a tablet, capsule, granules, or oral liquid. In one embodiment, the agomelatine (or a prodrug or salt thereof) is administered once daily (for example, in the form of a tablet). In another embodiment, 25 mg agomelatine (or a prodrug or salt thereof) is administered once daily (for example, in the form of an oral tablet). In another embodiment, 50 mg agomelatine (or a prodrug or salt thereof) is administered once daily (for example, in the form of an oral tablet). In one preferred embodiment, the dose is orally administered once daily at bedtime.

The amount of agomelatine (or a prodrug or salt thereof) administered may range from about 0.1 to about 150 mg/day, such as from about 0.1 to about 100 mg/day, from about 0.5 to about 50 mg/day, from about 1 to about 50 mg/day, or from about 1 to about 5 mg/day. In one embodiment, the daily dose of agomelatine (or a prodrug or salt thereof) is 25 mg per day to 50 mg per day and is preferably orally administered. In another embodiment, the daily dose of agomelatine (or a prodrug or salt thereof) is 25 mg per day and is orally administered. In yet another embodiment, the daily dose of agomelatine (or a prodrug or salt thereof) is 50 mg per day and is orally administered (e.g., at bedtime).

In one embodiment, treatment with 25 mg oral agomelatine once daily is initiated to treat the patient. In the event there is no improvement in symptoms, the dose may be increased to 50 mg oral agomelatine once daily. In one embodiment, liver function tests are performed in the patient when the daily dose is increased above 25 mg (such as to 50 mg). In another embodiment, liver function tests are performed in the patient before initiation of agomelatine treatment and before a daily dose increase to 50 mg. In one particular embodiment, treatment with agomelatine is not initiated if serum transaminase levels are greater than 2 times the upper limit of the normal range for the patient.

Patient Selection

In one embodiment, the EEG measurements are performed with electrodes placed according to the 10-20 system.

Example 1

The inventors conducted two parallel open-label clinical trials of agomelatine at 25 mg once at bedtime in patients with major depressive disorder (NCT05118750 and NCT05157945, whose data was pooled in these analyses). These patients were required to have moderate to severe depression and be on a stable and adequate dose of an antidepressant (in particular, an SSRI, SNRI, or bupropion) to which they had an inadequate treatment response (i.e., agomelatine treatment was an adjunct to the antidepressant). Patients were evaluated over the course of eight weeks of treatment.

EEG data were collected at rest (encompassing both eyes open and eyes closed conditions) prior to treatment using a 19-channel EEG system covering the conventional 10-20 electrode locations. A total of 107 patients with moderate to severe depression (MADRS≥20 and PHQ-9≥10) had EEG data (107 with eyes open (REO) EEG, 105 with eyes closed (REC) EEG). Quality control assessments were conducted, yielding 105 REO patient datasets and 103 REC patient datasets. These data were divided into a training dataset for identifying predictive signals, and a separate holdout dataset on which predictive signals could be additionally tested. The training dataset consisted of 60 REO patient datasets and 60 REC patient datasets. The holdout set consisted of 49 REO patient datasets and 46 REC patient datasets.

The brain is a dynamic system that is inherently nonlinear and complex. Statistical features derived from information theory and chaos theory, such as sample entropy and the Lyapunov exponent, may capture nonlinear aspects of systems that standard linear features fail to capture. This, in turn, can improve our ability to characterize EEG recordings and potentially differentiate disease-relevant brain patterns (Lau et al., *Eur J Neurosci*, 2022, 56 (7): 5047-5069, doi:

10.1111/ejn. 15800, PMID 35985344; Rodríguez-Bermúdez and García-Laencina, Appl. Math Inf. Sci. 9 (5): 2309-2321, 2015). Sample entropy, in particular, measures the irregularity of a system. Low sample entropy indicates low randomness, high regularity (i.e. repeating patterns), and implies high dependence between data points. High sample entropy, conversely, indicates high randomness, low regularity, and low dependence between data points (Delgado-Bonal and Marshak, *Entropy (Basel)*, 2019, 21 (6): 541, doi: 10.3390/e21060541, PMID: 33267255).

Sample entropy is a modified version of approximate entropy, which is a modification of the Kolmogorov-Sinai (KS) entropy (Delgado-Bonal and Marshak, 2019, supra). KS entropy directly relates to the "entropy rate" of a dynamic system, which measures how much information over time (on average) is needed to describe a process. However, KS entropy can only be practically calculated for well-defined systems without any measurement noise and vast amounts of data. Approximate entropy solves this problem with a basis in the same principles as KS entropy, but usable with real data (Pincus, PNAS, 1991, 88 (6): 2297-301, doi: 10.1073/pnas.88.6.2297, PMID: 11607165). Approximate entropy measures the frequency rate that a snippet of data of fixed length is approximately repeated and then also remains similar for the next sample. Approximate entropy is known to be biased measurement, especially with small amounts of data. Sample entropy is a very similar measure to approximate entropy but modified to solve this problem (Delgado-Bonal and Marshak, 2019, supra). Channel-wise EEG sample entropy was therefore calculated in the following analyses.

Figure 1B:
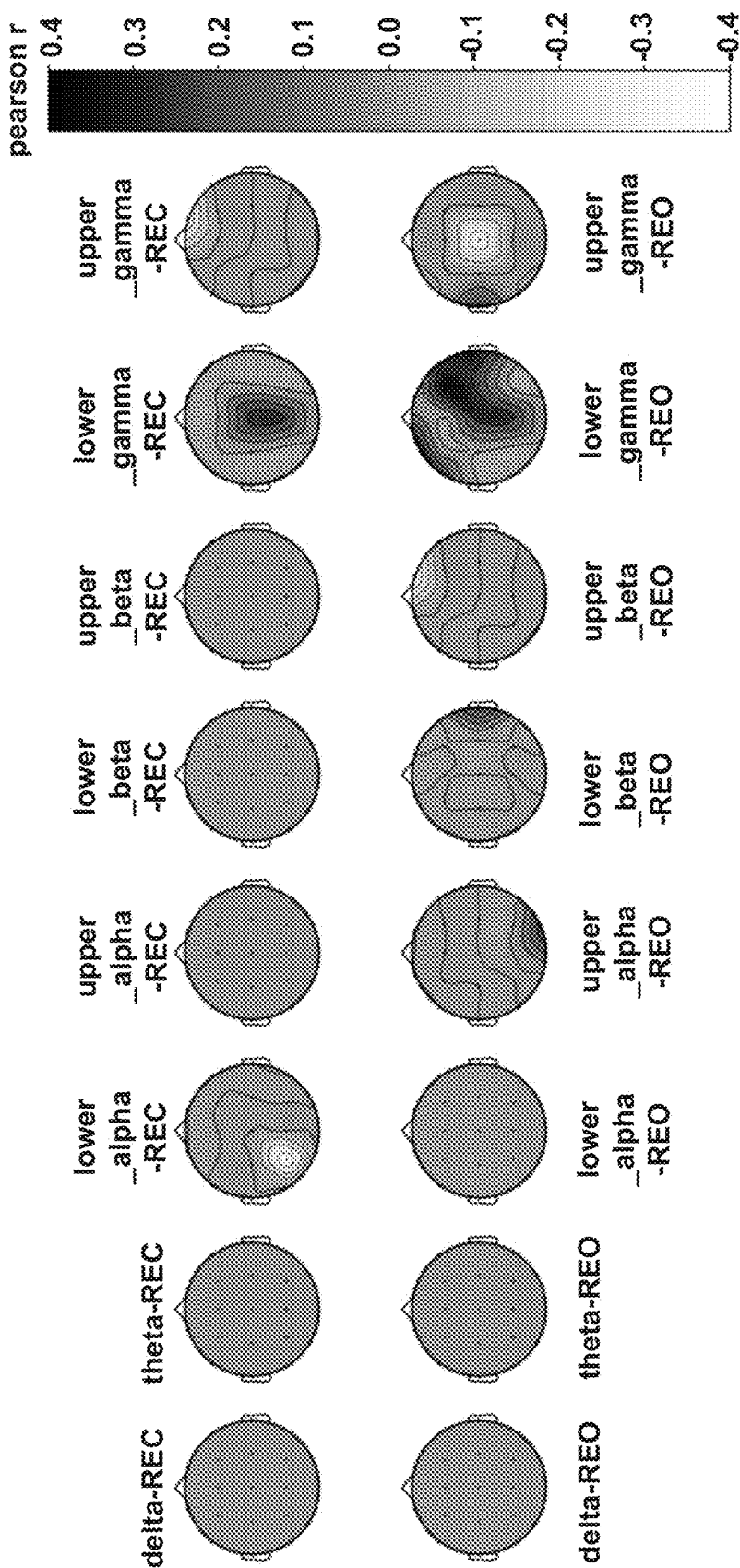
Figure 1C:
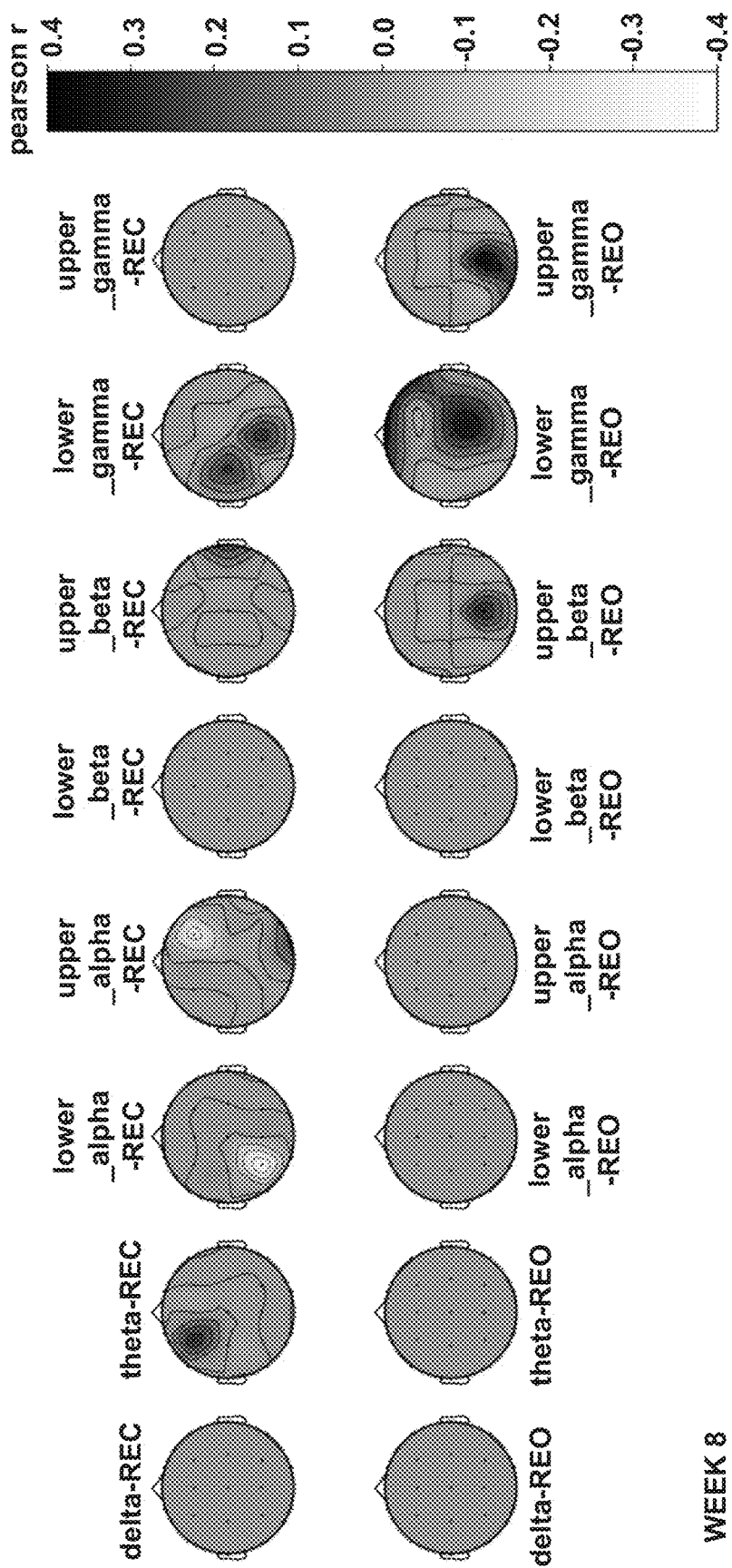

As seen in FIGS. 1A-1C (subsections A, B, and C), channel level sample entropy measures correlate at $p<0.05$ with percentage change in MADRS scores from baseline (to weeks 4, 6 and 8) across multiple frequency ranges and multiple scalp locations in the training dataset. In order to compile these individual signals into a single EEG composite entropy model for prediction of treatment outcome, the inventors conducted 10-fold cross-validated machine learning using elastic net regularization against an outcome of high versus low response to agomelatine. Cross-validation divides the training dataset iteratively into 9/10 for training the machine learning model and 1/10 for evaluating the predictive utility of the model (i.e., participants left out of the training itself, though part of the aforementioned training dataset). The training sample is then divided in this way until each participant has been left out of the training subset.

Figure 2A:
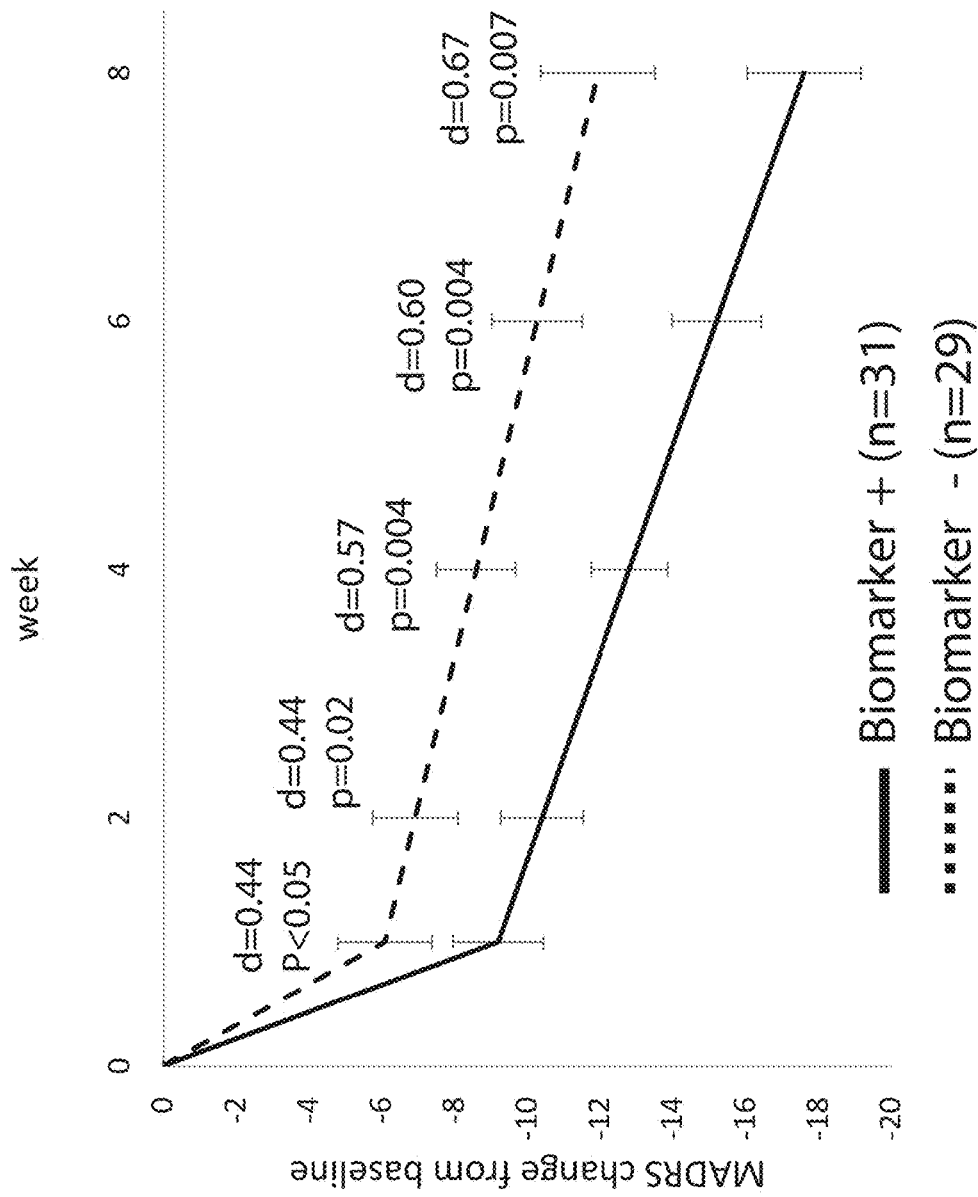
FIG. 2A shows a mixed model repeated measures (MMRM) analysis of change in MADRS scores in response to agomelatine between patients predicted by the EEG sample entropy machine learning model to respond to agomelatine. Data are plotted for patients left out of each round of model training during cross-validation. Also shown are one-sided p-values and Cohen's d effect sizes for the contrast between predicted responders and predicted non-responders.
Figure 2B:
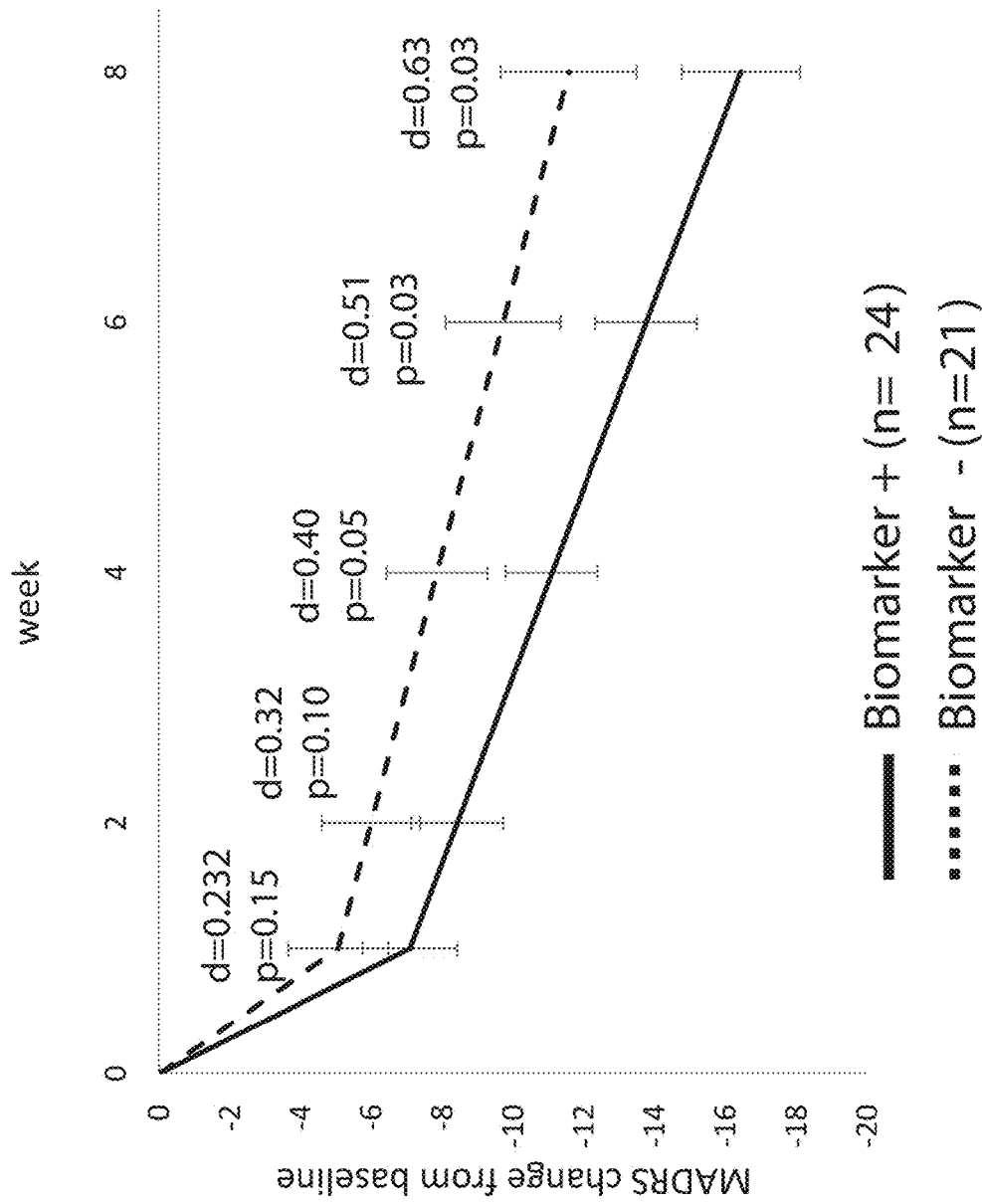
FIG. 2B shows a mixed model repeated measures (MMRM) analysis of change in MADRS scores in response to agomelatine between patients predicted by the EEG sample entropy machine learning model to respond to agomelatine. Data are plotted for the holdout test dataset, which contains participants not included in the training dataset and thus an independent test of replication. Also shown are one-sided p-values and Cohen's d effect sizes for the contrast between predicted responders and predicted non-responders.

FIG. 2A shows these cross-validation results for the left-out data within the training dataset, demonstrating statistically significant prediction of agomelatine outcome at all weeks of treatment. The Cohen's d effect sizes at these weeks are all >0.4, indicating a substantial effect size for the prediction, especially considering that the meta-analytically calculated all-comer (i.e., unselected depression patients) effect size for the difference in treatment response to agomelatine (as monotherapy) versus placebo is $d=0.26$ (Cipriani et al., *Lancet.*, 2018, 391 (10128): 1357-1366, PMID: 29477251). A similar pattern of effect sizes was seen in the holdout dataset, wherein the difference in predicted agomelatine responders versus non-responders with respect to observed change in MADRS scores was $d>0.4$ at weeks 4, 6 and 8. Statistical significance was achieved in the holdout test set for weeks 6 and 8 (see FIG. 2B), indicating replication of the prediction of agomelatine outcome by EEG sample entropy in an independent group of patients. Thus, it has been surprisingly discovered that an EEG complexity measure, in this case sample entropy, can predict which patient receiving adjunctive treatment with 25 mg of agomelatine will be more likely to see a reduction in depression symptoms. Notably, other measurements, such as chronobiology, sleep, and cognition, were not found predictive of whether adjunctive treatment with agomelatine would be effective at reducing depressive symptoms.

Figure 2C:
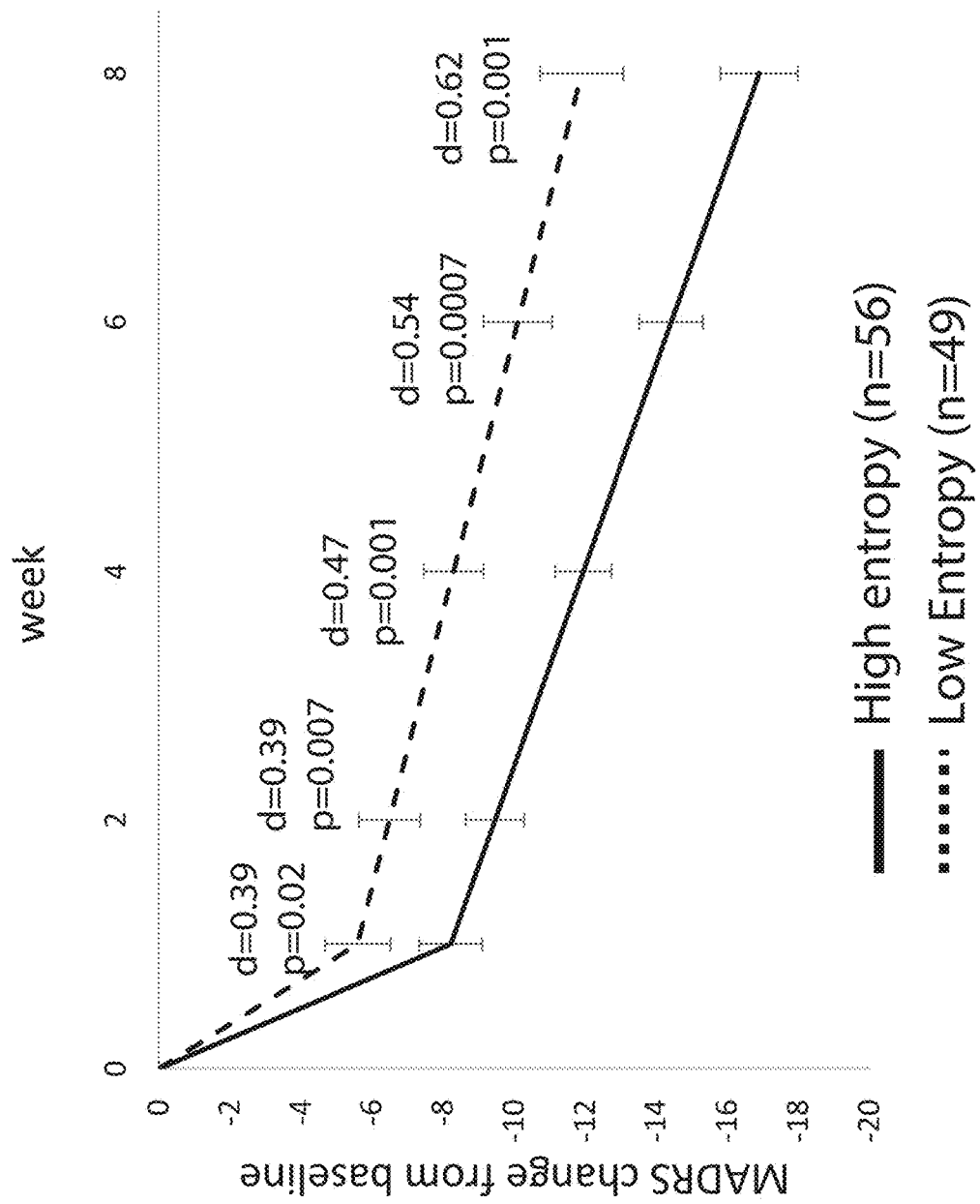
FIG. 2C shows a mixed model repeated measures (MMRM) analysis of change in MADRS scores in response to agomelatine between patients with high sample entropy at the Pz electrode using low gamma frequency range EEG. Data are plotted for the full sample, combining patients left out of each round of model training during cross-validation and those in the holdout dataset. Also shown are one-sided p-values and Cohen's d effect sizes for the contrast between predicted responders and predicted non-responders.

The inventors examined the weights ascribed by the machine learning model for each electrode, which revealed a prominent role for EEG sample entropy calculated at the Pz electrode on low gamma range frequency data (30-40 Hz). Plotted in FIG. 2C is the MADRS change of patients with high Pz-computed low-gamma sample entropy ($z \geq 0.27$ was used here) compared to those with low Pz low-gamma sample entropy in the full study sample, demonstrating strong and statistically significant prediction of treatment outcome across all weeks.

Figure 3A:
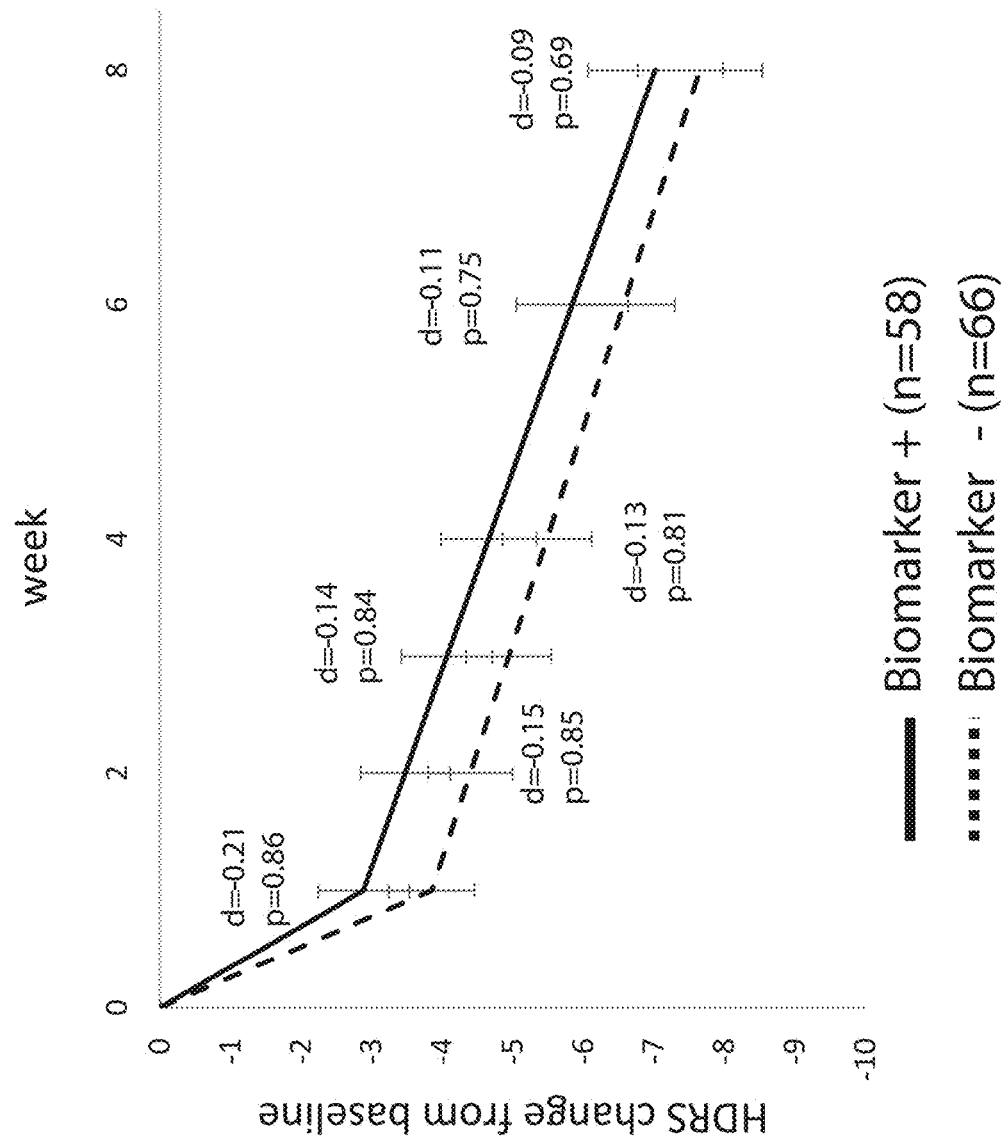
FIG. 3A shows a mixed model repeated measures (MMRM) analysis of change in MADRS scores in patients in the placebo arm of a randomized trial based on their predicted agomelatine response using the agomelatine EEG sample entropy machine learning model. Also shown are p-values and Cohen's d effect sizes for the contrast between predicted agomelatine responders and predicted non-responders with respect to observed response to placebo.
Figure 3B:
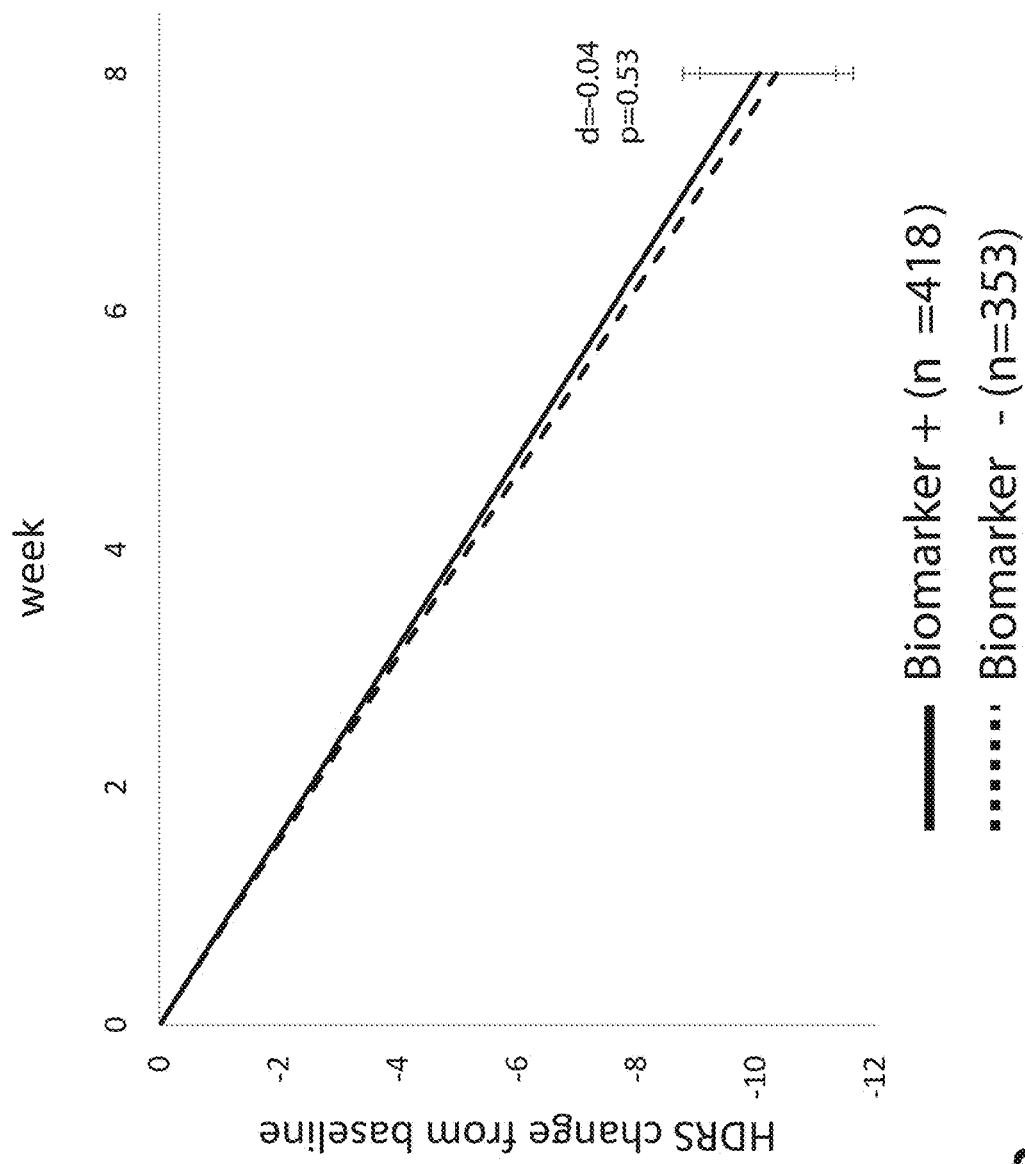
FIG. 3B shows a mixed model repeated measures (MMRM) analysis of change in MADRS scores in patients receiving a new SSRI or SNRI based on their predicted agomelatine response using the agomelatine EEG sample entropy machine learning model. Also shown are p-values and Cohen's d effect sizes for the contrast between predicted agomelatine responders and predicted non-responders with respect to observed response to SSRI/SNRIs.

In order to understand whether this machine learning model identifies patients who respond better to agomelatine as compared to either placebo or standard-of-care SSRIs or SNRIs, the inventors applied the EEG sample entropy machine learning model to EEG data from patients who went on to receive placebo treatment for 8 weeks as part of a randomized trial in depression (Trivedi et al., *J Psychiatr Res.*, 2016, 78:11-23, PMID: 27038550). As shown in FIG. 3A, there is no significant difference between patients predicted by the EEG model to respond better or worse to agomelatine with respect to how they responded to placebo. In fact, these data demonstrate a slight effect in the opposite direction, whereby predicted agomelatine responders did numerically more poorly when given placebo. In a similar manner, patients who were given a new SSRI or SNRI showed no difference in outcome over 8 weeks when divided based on the agomelatine EEG model (FIG. 3B). Highly similar results were seen if using Pz signal only instead of the full machine learning model, also with a numerical superiority for low entropy patients (i.e., predicted agomelatine non-responders) in terms of response to placebo or SSRI/SNRIs. Thus, these data demonstrate the specificity of the EEG sample entropy model for predicting outcome with agomelatine, yielding therefore a novel and non-obvious tool for identifying who should and who should not receive agomelatine for the treatment of depression. Surprisingly, sample entropy at a single electrode in the low gamma frequency range (i.e., Pz) was able to robustly and specifically predict agomelatine outcome.

Given the approximate 50% prevalence of positivity on the EEG machine learning model, one can estimate the agomelatine-placebo difference in EEG-predicted agomelatine responders by adding the all-comer effect size ($d=0.26$) to the enrichment in EEG-predicted responders over the all-comer population. This enrichment is calculated by halving the effect size between EEG-predicted responders and non-responders, since the average of these two groups is the all-comer population. No difference in placebo response as a function of EEG-predicted agomelatine response was assumed in the calculation (a conservative assumption in light of the results in FIG. 3A). Doing the calculations above, using the full sample effect size shown in FIG. 2B implies an agomelatine-placebo response in EEG-predicted responders of $d=0.58$ at week 8, which is more than double the all-comer effect size previously observed with agomelatine monotherapy in depression (i.e. all corner without the benefit of a treatment-predictive signal). Likewise, the implied agomelatine-placebo difference for EEG-predicted non-responders is $d=-0.06$, suggesting no difference at all between agomelatine monotherapy and placebo in patients predicted not to respond based on EEG sample entropy. Very similar results were obtained using Pz low gamma sample entropy alone (d=0.51 in high entropy patients and d=0.0 in low entropy patients based on the full sample results). Thus, there is clear clinical utility of EEG agomelatine-predictive signals, with benefit of the drug only accruing to patients predicted to respond to agomelatine and no benefit for patients predicted to not respond based on EEG.

In addition to sample entropy, the inventors developed similar machine learning models to test the predictive utility of a range of other EEG complexity measures, as well as other common EEG indices. As seen in Tables 1A and 1B below (significant results are bolded; uncorrected p-values are provided), significant prediction of agomelatine outcome was achieved by use of several other measures of complexity (approximate entropy, detrended fluctuation analysis, Higuchi fractal dimension, Katz fractal dimension, largest Lyapunov exponent, modified multiscale entropy, multiscale entropy, and aperiodic exponent). No significant prediction of agomelatine outcome was achieved with several complexity measures that were used, including Lempel-Ziv complexity, permutation entropy and Tsallis entropy. Thus, certain complexity measures appear to carry consistent and strong prediction of agomelatine outcome. Another measure, the aperiodic exponent, which is sensitive to the balance between excitation and inhibition and may have some relationship to complexity (Park et al., *Front Comput Neurosci.*, 2023, 17:1169288, PMID: 37122995; Deco et al., *J Neurosci.*, 2014, 34 (23): 7886-98, PMID: 24899711; Donoghue et al., *Nat Neurosci.*, 2020, 23 (12): 1655-1665, PMID: 33230329), is also predictive (significant at week 4). However, a common EEG index such as relative power is not predictive.

TABLE 1A

| Eye condition | Model Type | Frequency | Week 1 d | Week 1 p | Week 2 d | Week 2 p | Week 4 d | Week 4 p |
|---|---|---|---|---|---|---|---|---|
| REO | Approximate Entropy | lower gamma | −0.15 | 0.555 | −0.05 | 0.782 | 0.09 | 0.630 |
| REC | Approximate Entropy | lower gamma | 0.23 | 0.362 | 0.29 | 0.172 | 0.46 | 0.027 |
| REO | Detrended Fluctuation Analysis | lower beta | 0.03 | 0.916 | 0.06 | 0.777 | 0.12 | 0.520 |
| REO | Detrended Fluctuation Analysis | delta | 0.07 | 0.793 | 0.10 | 0.621 | 0.18 | 0.346 |
| REC | Detrended Fluctuation Analysis | upper beta | 0.19 | 0.427 | 0.20 | 0.331 | 0.25 | 0.216 |
| REO | Detrended Fluctuation Analysis | upper gamma | 0.37 | 0.137 | 0.33 | 0.099 | 0.32 | 0.079 |
| REC | Detrended Fluctuation Analysis | lower beta | 0.49 | 0.047 | 0.44 | 0.035 | 0.41 | 0.038 |
| REC | Higuchi Fractal Dimension | upper beta | −0.29 | 0.244 | −0.20 | 0.349 | −0.05 | 0.785 |
| REO | Higuchi Fractal Dimension | lower beta | 0.03 | 0.898 | 0.03 | 0.860 | 0.05 | 0.797 |
| REO | Higuchi Fractal Dimension | upper gamma | 0.04 | 0.885 | 0.06 | 0.767 | 0.11 | 0.551 |
| REO | Higuchi Fractal Dimension | delta | −0.15 | 0.541 | −0.05 | 0.809 | 0.12 | 0.527 |
| REC | Higuchi Fractal Dimension | upper gamma | 0.16 | 0.529 | 0.16 | 0.433 | 0.21 | 0.307 |
| REC | Higuchi Fractal Dimension | lower beta | 0.44 | 0.073 | 0.36 | 0.080 | 0.28 | 0.161 |
| REC | Higuchi Fractal Dimension | lower gamma | 0.64 | 0.012 | 0.58 | 0.006 | 0.57 | 0.005 |
| REO | Katz Fractal Dimension | lower beta | 0.28 | 0.249 | 0.18 | 0.351 | 0.06 | 0.769 |
| REO | Katz Fractal Dimension | delta | 0.04 | 0.867 | 0.07 | 0.733 | 0.13 | 0.494 |
| REC | Katz Fractal Dimension | lower gamma | 0.25 | 0.312 | 0.23 | 0.272 | 0.23 | 0.256 |
| REC | Katz Fractal Dimension | upper gamma | 0.04 | 0.864 | 0.10 | 0.631 | 0.23 | 0.262 |
| REO | Katz Fractal Dimension | upper beta | 0.24 | 0.313 | 0.24 | 0.219 | 0.29 | 0.123 |
| REC | Katz Fractal Dimension | lower beta | 0.47 | 0.057 | 0.42 | 0.049 | 0.37 | 0.067 |
| REC | Katz Fractal Dimension | upper beta | 0.42 | 0.082 | 0.40 | 0.054 | 0.42 | 0.039 |
| REO | Largest Lyapunov Exponent | upper gamma | −0.24 | 0.323 | −0.11 | 0.569 | 0.08 | 0.651 |
| REO | Largest Lyapunov Exponent | upper alpha | 0.03 | 0.893 | 0.08 | 0.690 | 0.17 | 0.347 |
| REC | Largest Lyapunov Exponent | upper alpha | 0.10 | 0.692 | 0.12 | 0.566 | 0.18 | 0.371 |
| REC | Largest Lyapunov Exponent | upper gamma | −0.02 | 0.932 | 0.08 | 0.698 | 0.29 | 0.159 |
| REO | Lempel-Ziv Complexity | lower gamma | −0.24 | 0.324 | −0.13 | 0.501 | 0.02 | 0.894 |
| REC | Lempel-Ziv Complexity | upper alpha | 0.21 | 0.389 | 0.17 | 0.408 | 0.13 | 0.532 |

TABLE 1A-continued

| Eye condition | Model Type | Frequency | Week 1 d | Week 1 p | Week 2 d | Week 2 p | Week 4 d | Week 4 p |
|---|---|---|---|---|---|---|---|---|
| REC | Lempel-Ziv Complexity | lower gamma | −0.06 | 0.806 | 0.01 | 0.955 | 0.15 | 0.462 |
| REO | Lempel-Ziv Complexity | theta | 0.13 | 0.587 | 0.14 | 0.494 | 0.17 | 0.367 |
| REO | Lempel-Ziv Complexity | upper beta | 0.19 | 0.426 | 0.21 | 0.283 | 0.30 | 0.126 |
| REC | Modified Multiscale Entropy | lower alpha | 0.08 | 0.743 | 0.11 | 0.591 | 0.19 | 0.349 |
| REC | Modified Multiscale Entropy | lower gamma | −0.09 | 0.711 | 0.01 | 0.958 | 0.21 | 0.313 |
| REO | Modified Multiscale Entropy | upper beta | 0.08 | 0.736 | 0.15 | 0.435 | 0.31 | 0.093 |
| REC | Modified Multiscale Entropy | upper alpha | 0.19 | 0.428 | 0.25 | 0.225 | 0.39 | 0.045 |
| REO | Multiscale Entropy | lower gamma | −0.41 | 0.096 | −0.21 | 0.263 | 0.05 | 0.797 |
| REC | Multiscale Entropy | upper alpha | 0.05 | 0.833 | 0.08 | 0.701 | 0.15 | 0.472 |
| REO | Multiscale Entropy | upper beta | −0.09 | 0.729 | 0.02 | 0.924 | 0.20 | 0.277 |
| REC | Multiscale Entropy | lower gamma | 0.18 | 0.488 | 0.24 | 0.287 | 0.39 | 0.080 |
| REC | Permutation Entropy | lower gamma | 0.38 | 0.119 | 0.35 | 0.098 | 0.33 | 0.105 |
| REO | Tsallis Entropy | lower beta | −0.18 | 0.490 | −0.09 | 0.642 | 0.02 | 0.909 |
| REC | Tsallis Entropy | upper alpha | 0.03 | 0.904 | 0.04 | 0.848 | 0.06 | 0.745 |
| REO | Tsallis Entropy | lower gamma | 0.21 | 0.441 | 0.18 | 0.413 | 0.16 | 0.421 |

TABLE 1B

| Eye condition | Model Type | Frequency | Week 6 d | Week 6 p | Week 8 d | Week 8 p |
|---|---|---|---|---|---|---|
| REO | Approximate Entropy | lower gamma | 0.22 | 0.284 | 0.35 | 0.171 |
| REC | Approximate Entropy | lower gamma | 0.54 | 0.010 | 0.69 | 0.011 |
| REO | Detrended Fluctuation Analysis | lower beta | 0.18 | 0.397 | 0.23 | 0.367 |
| REO | Detrended Fluctuation Analysis | delta | 0.26 | 0.244 | 0.32 | 0.229 |
| REC | Detrended Fluctuation Analysis | upper beta | 0.27 | 0.211 | 0.29 | 0.257 |
| REO | Detrended Fluctuation Analysis | upper gamma | 0.32 | 0.126 | 0.31 | 0.220 |
| REC | Detrended Fluctuation Analysis | lower beta | 0.35 | 0.099 | 0.31 | 0.232 |
| REC | Higuchi Fractal Dimension | upper beta | 0.08 | 0.707 | 0.20 | 0.433 |
| REO | Higuchi Fractal Dimension | lower beta | 0.06 | 0.778 | 0.07 | 0.786 |
| REO | Higuchi Fractal Dimension | upper gamma | 0.16 | 0.451 | 0.20 | 0.431 |
| REO | Higuchi Fractal Dimension | delta | 0.26 | 0.195 | 0.41 | 0.105 |
| REC | Higuchi Fractal Dimension | upper gamma | 0.22 | 0.293 | 0.25 | 0.334 |
| REC | Higuchi Fractal Dimension | lower beta | 0.17 | 0.407 | 0.09 | 0.721 |
| REC | Higuchi Fractal Dimension | lower gamma | 0.50 | 0.019 | 0.47 | 0.076 |
| REO | Katz Fractal Dimension | lower beta | −0.07 | 0.742 | −0.18 | 0.469 |
| REO | Katz Fractal Dimension | delta | 0.18 | 0.387 | 0.23 | 0.366 |
| REC | Katz Fractal Dimension | lower gamma | 0.20 | 0.338 | 0.19 | 0.458 |
| REC | Katz Fractal Dimension | upper gamma | 0.32 | 0.134 | 0.43 | 0.108 |
| REO | Katz Fractal Dimension | upper beta | 0.32 | 0.124 | 0.35 | 0.165 |

TABLE 1B-continued

| Eye condition | Model Type | Frequency | Week 6 d | Week 6 p | Week 8 d | Week 8 p |
|---|---|---|---|---|---|---|
| REC | Katz Fractal Dimension | lower beta | 0.29 | 0.172 | 0.24 | 0.362 |
| REC | Katz Fractal Dimension | upper beta | 0.39 | 0.072 | 0.36 | 0.150 |
| REO | Largest Lyapunov Exponent | upper gamma | 0.26 | 0.208 | 0.43 | 0.092 |
| REO | Largest Lyapunov Exponent | upper alpha | 0.26 | 0.210 | 0.34 | 0.179 |
| REC | Largest Lyapunov Exponent | upper alpha | 0.22 | 0.307 | 0.26 | 0.314 |
| REC | Largest Lyapunov Exponent | upper gamma | 0.46 | 0.037 | 0.62 | 0.019 |
| REO | Lempel-Ziv Complexity | lower gamma | 0.17 | 0.411 | 0.31 | 0.225 |
| REC | Lempel-Ziv Complexity | upper alpha | 0.07 | 0.743 | 0.02 | 0.927 |
| REC | Lempel-Ziv Complexity | lower gamma | 0.26 | 0.226 | 0.37 | 0.156 |
| REO | Lempel-Ziv Complexity | theta | 0.19 | 0.352 | 0.22 | 0.389 |
| REO | Lempel-Ziv Complexity | upper beta | 0.35 | 0.098 | 0.40 | 0.113 |
| REC | Modified Multiscale Entropy | lower alpha | 0.24 | 0.260 | 0.30 | 0.253 |
| REC | Modified Multiscale Entropy | lower gamma | 0.37 | 0.089 | 0.54 | 0.044 |
| REO | Modified Multiscale Entropy | upper beta | 0.43 | 0.028 | 0.61 | 0.020 |
| REC | Modified Multiscale Entropy | upper alpha | 0.51 | 0.018 | 0.62 | 0.018 |
| REO | Multiscale Entropy | lower gamma | 0.30 | 0.160 | 0.52 | 0.040 |
| REC | Multiscale Entropy | upper alpha | 0.20 | 0.375 | 0.24 | 0.360 |
| REO | Multiscale Entropy | upper beta | 0.36 | 0.075 | 0.54 | 0.037 |
| REC | Multiscale Entropy | lower gamma | 0.49 | 0.040 | 0.57 | 0.039 |
| REC | Permutation Entropy | lower gamma | 0.27 | 0.197 | 0.24 | 0.351 |
| REO | Tsallis Entropy | lower beta | 0.13 | 0.542 | 0.23 | 0.375 |
| REC | Tsallis Entropy | upper alpha | 0.08 | 0.699 | 0.10 | 0.696 |
| REO | Tsallis Entropy | lower gamma | 0.15 | 0.518 | 0.13 | 0.634 |

Figure 4:
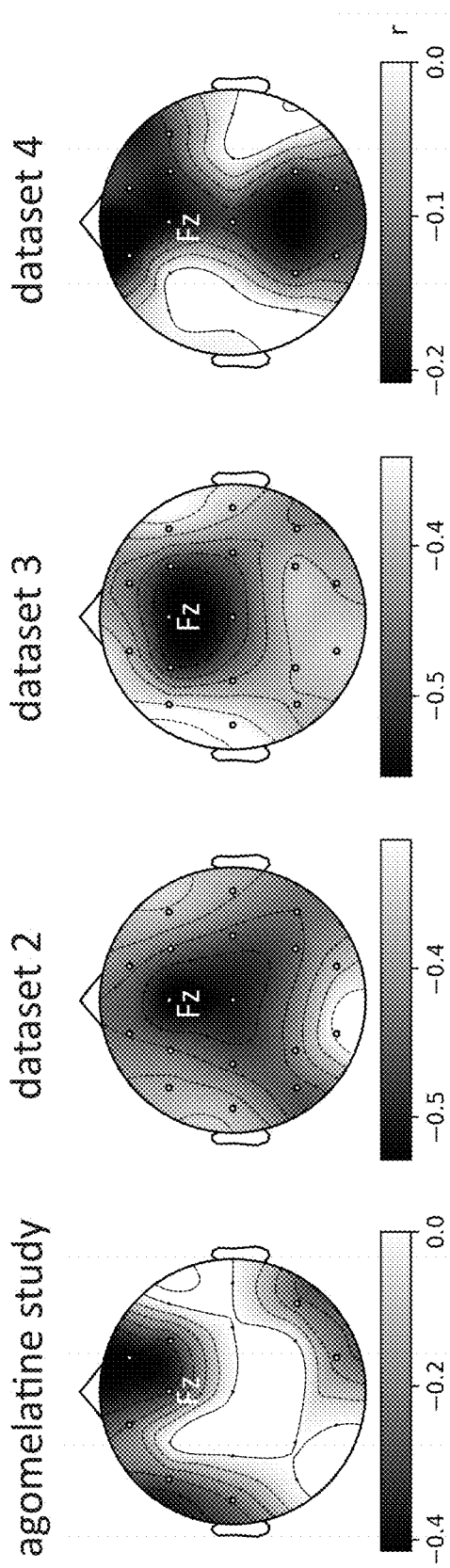
FIG. 4 shows a $p<0.05$ thresholded topographical map of channel-level correlations between Pz low gamma sample entropy and low gamma power envelope connectivity between Pz and each other electrode (REC). Datasets shown are baseline EEG data from the agomelatine trial (left-most, N=117), as well as baseline data from three other studies in depression (from second from the left to the right: dataset 1 N=894, dataset 2 N=793, dataset 3 N=215).

Having found that higher EEG sample entropy predicts better agomelatine response, the inventors reasoned that EEG signal that is more erratic, unpredictable and irregular (i.e. higher entropy) may result in poorer information transfer between a brain region with these attributes and other brain regions. Information transfer in EEG can be tested using measures of connectivity, such as orthogonalized power envelope connectivity (Hipp et al., *Nat Neurosci.*, 2012, 15 (6): 884-90, PMID: 22561454). The inventors therefore examined whether higher Pz low gamma frequency entropy could predict lower power envelope connectivity from Pz. As seen in FIG. 4, higher low gamma Pz sample entropy predicted lower Pz connectivity in particular to midline frontal regions (e.g., at electrode Fz). The location of this electrode suggests that the decrease in connectivity impacts the default mode network in the brain, a neural network identified as having a central role in depression (Runia et al., *Neruosci Biobehav Rev.*, 2022, 132:433-438, PMID: 34890601; Tozzi et al., *Neuroimage Clin.*, 2021, 30:102570; PMID: 33540370). Thus, measures of connectivity, inasmuch as they reflect the correlates of entropy, can also be used to identify agomelatine responders versus non-responders.

Example 2

A randomized, double-blind, placebo-controlled clinical trial of agomelatine in adults with MDD is on-going. The study includes adult patients (aged 18 to <71 years old) with moderate to severe MDD that meet the inclusion criteria and exclusion criteria below. The study is a 6-week, multicenter, double-blind (DB), placebo-controlled clinical trial of 25 mg agomelatine once nightly as an adjunctive add-on treatment for adults with MDD who are currently taking another prescribed antidepressant with an inadequate response (<50% improvement on the current treatment). Participants will continue taking their current antidepressant throughout the study without changing dose during the screening and double-blind portion of the study unless for safety reasons. Prior to taking the study medication, participants will be screened for a brain-based enrichment marker (based on electroencephalography (EEG), computerized neurocognitive tests, and/or wearable behavior tracking data) and subdivided into biomarker subgroups for data analysis. Participants and site staff will be blinded to biomarker status to minimize bias. An enrichment strategy will be used to assess efficacy of adjunctive agomelatine versus placebo for treating depression based on the biomarker of interest. The study goals are to validate biomarker(s) that can be used to predict any patient's likelihood to respond to agomelatine in an individualized or personalized manner (precision psychiatry).

After a screening period and collection of baseline biomarkers, study participants will be randomized in a 1:1 ratio based on gender and enrichment marker status for the DB period to either 25 mg agomelatine once nightly or a matched placebo and followed for 6 weeks, consisting of five study visits including Day 1 when study intervention is started. Participants who complete dosing of the study intervention during the DB period may enter an optional 8-week open-label (OL) period to take (unblinded) 25 mg agomelatine once nightly, and with 4 additional visits. Unblinding of the DB intervention will not occur between the DB and OL visits. After participants complete the OL period, or at the end of the DB period for those who do not enter the OL period, or after any early discontinuation of study drug for those choosing not to continue in the study, there will be an end of period (EOP) visit followed by a safety follow-up visit (FUV) approximately one week later. If a participant discontinues their study intervention before the treatment period has ended, they may choose to complete the remaining visits from that period (DB or OL) including the FUV. Participants who discontinue study intervention during the DB period may not enter the OL period.

Approximately 200 participants will be randomized and stratified by gender and biomarker status and treated in the DB period. Approximately 1000 participants (up to 1250 screened is allowed) will need to be screened to reach 200 randomized participants.

Inclusion Criteria: To be eligible to participate in this study, an individual must meet all of the following criteria:
  age must be 18 to <71 years old.
  have a diagnosis of MDD based on the SCID-5 and:
    have moderate to severe depression on DSM-5 depression criteria items, as assessed by a score of ≥10 on the PHQ-9.
    have moderate to severe MDD as confirmed by MADRS total score ≥22 administered by the MGH-CTNI remote rater before agomelatine treatment and pass the SAFER interview.
  taking a stable dose of a single antidepressant, which may be an SSRI (other than fluvoxamine), SNRI, or bupropion (participants need to be taking the antidepressant at least 5 days per week during screening, though full adherence is preferred).
  have been on that antidepressant for ≥6 weeks at an adequate dosage defined by the Antidepressant Treatment Response Questionnaire (ATRQ), with no modification to dosage for ≥2 weeks.
  have a response to their currently prescribed antidepressant of <50% improvement as defined by the ATRQ.
  based on clinical assessment have either:
    had a period of remission of at least 2 consecutive months (not meeting DSM-5 criteria for MDD) in the past 26 months, regardless of the number of failed antidepressants, or
    did not have a period of remission of at least 2 consecutive months in the past 26 months and within the past 24 months have not failed >3 antidepressants (including current antidepressant) at an adequate dosage and duration as defined by the ATRQ.
  Body mass index (BMI) ≥17 and ≤41
  male and/or females who are not pregnant, breastfeeding or planning to get pregnant or father a child while on study medication and for a period of 60 days after study completion.

Exclusion Criteria: Participants are excluded from the study if any of the following criteria apply:
Medical Condition
  1. Any of the following medical conditions:
    hepatic impairment (i.e., cirrhosis or active/chronic liver disease).
    baseline serum transaminase (aspartate transaminase (AST) or alanine transaminase (ALT)) levels that exceed 2×ULN.
    pregnant or breastfeeding or planning to become pregnant.
    severe impediment to vision, hearing, comprehension, and/or hand movement that interferes with study tasks.
    any contraindications to EEG (i.e., requiring high concentration oxygen).
    active suicidal ideation as determined by either the CHRT-SR12 score of 3 (agree) or 4 (strongly agree) on items 11 or 12 or investigator assessment based on results from the CHRT-C and/or clinical assessment.
    moderate to severe Alcohol Use Disorder (AUD) or current moderate or severe substance use disorder (SUD), other than nicotine, is exclusionary determined by clinical assessment. SUD in remission for 3 months is acceptable.
    clinically significant history or evidence of acute or unstable cardiovascular, respiratory, renal, gastrointestinal, endocrine, neurological (such as in the past year: seizure, cerebral vascular disease, traumatic brain injury), immunological, or other major disease as determined by the site investigator. Stable, chronic medical illnesses are allowed.
    gastric bypass, gastric lap band, and/or gastric sleeve in the past year, due to the potential failure to absorb and metabolize the investigational product completely and safely.
Prior/Concomitant Therapy
  2. Concurrent use of any of the following:
    monoamine oxidase inhibitors (MAOIs)
    are on more than one current antidepressant other than low-dose trazodone (≤100 mg/d) taken no more than 3 days per week
    atomoxetine, viloxazine, or mirtazapine
    melatonin, ramelteon, or other melatonin agonist (including dietary supplements that contain melatonin)
    a potent CYP1A2 inhibitor (e.g., fluvoxamine and ciprofloxacin)
    mood stabilizers (anticonvulsants for non-psychiatric reasons may be allowed with Sponsor's permission)
    antipsychotic medications
    benzodiazepines, stimulants, or opiate pain medications greater than 3 days per week and unable to reduce use to 3 or fewer days per week on an as needed basis. These medications may not be used for 24 hours before a biomarker assessment.
    Hypnotic (including trazodone) medications greater than three days per week and unable to reduce use to three or fewer days per week on an as needed basis and not taken for 24 hours before biomarker assessments.

Note: Medications may be modified to meet inclusion criteria if clinically indicated. Medications should be discontinued long enough before agomelatine treatment to ensure no withdrawal symptoms are present.

3. Have received electroconvulsive therapy (ECT), deep brain stimulation (DBS), vagus nerve stimulation (VNS), >2 treatments with ketamine or esketamine in the current depressive episode (a new depressive episode occurs if someone does not meet DSM-5 criteria for MDD for two consecutive months).
4. Unstable psychotherapy as defined by a change in frequency and/or type of individual or group therapy in the 6 weeks prior to agomelatine treatment if the frequency is ≤2x/month or in the last 3 months if the therapy is >2x/month (approximately weekly).

Prior/Concurrent Clinical Study Experience

5. Receipt of any other central nervous system (CNS) investigational medication or investigational device within 6 months of the first study visit and more than one CNS interventional trial in the past 12 months. Non-CNS interventional trials or CNS observational trials may be allowed in the past 6 to 12 months after review with the Sponsor.
6. Prior participation in a study with ALTO-300 or agomelatine.

Diagnostic Assessments

7. Diagnosis of bipolar disorder or a psychotic disorder or symptoms based on the SCID for DSM-5.
8. Diagnosis of dementia based on history or clinical assessment.
9. Significant current PTSD symptoms based on PCL-5 >50 initially.

Other Exclusions

10. Positive urine toxicology (not including marijuana or documented prescription). One retest during screening is allowed. Current moderate or severe substance use disorder (SUD) (other than nicotine) determined by clinical assessment is exclusionary. Participants with a history of SUDs need to be in remission for at least 3 months prior to study initiation.
11. Excessive use of alcohol defined by (on average)>21 standard drinks/week for males and >14 standard drinks/week for females.
12. Known hypersensitivity to agomelatine, its components, or any of the excipients used in the formulation.
13. Employees/family of employees of clinic site.
14. Any other condition and/or situation that the investigator believes may interfere with the safety of the participant, study conduct, or interpretation of study data.

Lifestyle Considerations

No use of drugs of abuse except for limited amounts of *cannabis* (any form, up to 3 days per week and not meeting criteria for SUD) is permitted during study participation.

Participants are asked to follow the Centers for Disease Control and Prevention (CDC) recommendations for alcohol consumption: 1 standard drink per day (averaged over a week) for females and 2 standard drinks per day (averaged over a week) for males. Limitations on concomitant medication are described in Section 6.5.

*Cannabis* and alcohol should not be used 24 hours prior to any study visit.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

The invention claimed is:

1. A method of treating major depressive disorder in a patient,
where the patient is being treated with an antidepressant other than agomelatine but has failed to adequately respond to the antidepressant, the method comprising:
(a) measuring EEG sample entropy in the 30-40 Hz frequency range in the patient; and
(b) upon the patient being determined to be responsive to agomelatine based on having high EEG sample entropy, administering to the patient an effective amount of (i) agomelatine or a pharmaceutically acceptable salt thereof and (ii) the antidepressant.

2. The method of claim 1, wherein prior to initiation of treatment with agomelatine, the patient had a response to the antidepressant of <50% as defined by the Antidepressant Treatment Response Questionnaire (ATRQ).

3. The method of claim 1, wherein for at least 2 weeks prior to agomelatine treatment, no modification was made to the dosage of the antidepressant.

4. The method of claim 1, wherein the antidepressant is selected from a selective serotonin reuptake inhibitor, serotonin norepinephrine reuptake inhibitor, bupropion or a pharmaceutically acceptable salt thereof, or any combination of any of the foregoing.

5. The method of claim 4, wherein the antidepressant is selected from a selective serotonin reuptake inhibitor, serotonin norepinephrine reuptake inhibitor, or bupropion or a pharmaceutically acceptable salt thereof.

6. The method of claim 4, wherein the selective serotonin reuptake inhibitor is not fluvoxamine.

7. The method of claim 1, wherein the sample entropy in step (a) is analyzed with stored historical subject data containing data from a plurality of subjects having major depressive disorder, who received treatment with agomelatine or a pharmaceutically acceptable salt thereof, wherein the data include for a plurality of the subjects, the efficacy of the agomelatine treatment and sample entropy measured in the patient.

8. The method of claim 7, wherein step (a) comprises determining an agomelatine efficacy likelihood score for the patient based on the stored historical subject data; and step (b) comprises administering to the patient an effective amount of agomelatine or a pharmaceutically acceptable salt thereof, where the patient is determined to be responsive to agomelatine based on the likelihood score.

9. The method of claim 1, wherein in step (b), the patient is considered responsive to agomelatine based on a high EEG sample entropy at the Pz electrode according to the 10-20 system of electrode placement.

10. The method of claim 1, wherein the patient suffers from moderate to severe major depressive disorder.

11. The method of claim 1, wherein step (b) comprises, upon the patient being determined to be responsive to agomelatine based on having high EEG sample entropy, orally administering from about 25 to about 50 mg agomelatine per day.

12. The method of claim 11, wherein step (b) comprises, upon the patient being determined to be responsive to agomelatine based on having high EEG sample entropy, orally administering about 25 mg agomelatine per day.

13. The method of claim 11, wherein step (b) comprises, upon the patient being determined to be responsive to agomelatine based on having high EEG sample entropy, orally administering about 30 mg agomelatine per day.

14. The method of claim 11, wherein step (b) comprises, upon the patient being determined to be responsive to agomelatine based on having high EEG sample entropy, orally administering about 50 mg agomelatine per day.

15. The method of claim 11, wherein the agomelatine is administered once daily nightly.

16. A method of treating major depressive disorder in a patient, where the patient is being treated with an antidepressant other than agomelatine but has failed to adequately respond to the antidepressant, the method comprising:
- (a) measuring EEG sample entropy in the 30-40 Hz frequency range at the Pz electrode in the patient;
- (b) upon the patient having high EEG sample entropy, administering to the patient an effective amount of (i) agomelatine or a pharmaceutically acceptable salt thereof and (ii) the antidepressant; and
- (c) upon the patient having low EEG sample entropy, not initiating treatment with agomelatine or a pharmaceutically acceptable salt thereof.

17. The method of claim 16, wherein in step (b), from about 25 to about 50 mg agomelatine is orally administered per day.

\* \* \* \* \*